US009796973B2

(12) United States Patent
Akada et al.

(10) Patent No.: US 9,796,973 B2
(45) Date of Patent: Oct. 24, 2017

(54) TERMINATOR SEQUENCE-CONTAINING REVERSE PRIMER FOR OVEREXPRESSION AND LINEAR DNA

(75) Inventors: Rinji Akada, Ube (JP); Hisashi Hoshida, Ube (JP); Mikiko Nakamura, Ube (JP)

(73) Assignee: YAMAGUCHI UNIVERSITY, Yamaguchi (JP)

( * ) Notice: Subject to any disclaimer, the term of this patent is extended or adjusted under 35 U.S.C. 154(b) by 0 days.

(21) Appl. No.: 14/113,674

(22) PCT Filed: Apr. 27, 2012

(86) PCT No.: PCT/JP2012/002936
§ 371 (c)(1),
(2), (4) Date: Feb. 26, 2014

(87) PCT Pub. No.: WO2012/147370
PCT Pub. Date: Nov. 1, 2012

(65) Prior Publication Data
US 2014/0179002 A1 Jun. 26, 2014

(30) Foreign Application Priority Data
Apr. 28, 2011 (JP) .................................. 2011-101015

(51) Int. Cl.
| C12N 15/113 | (2010.01) |
| C12N 15/64 | (2006.01) |
| C12N 15/10 | (2006.01) |
| C12N 15/85 | (2006.01) |
| C12N 15/11 | (2006.01) |

(52) U.S. Cl.
CPC ........ *C12N 15/113* (2013.01); *C12N 15/1075* (2013.01); *C12N 15/111* (2013.01); *C12N 15/64* (2013.01); *C12N 15/85* (2013.01); *C12N 2310/531* (2013.01); *C12N 2330/51* (2013.01)

(58) Field of Classification Search
None
See application file for complete search history.

(56) References Cited

U.S. PATENT DOCUMENTS

| 6,040,174 A | 3/2000 | Imler et al. |
| 2002/0037525 A1 | 3/2002 | Liang et al. |
| 2002/0146733 A1 | 10/2002 | Sykes et al. |
| 2003/0185890 A1 | 10/2003 | Zuckermann et al. |
| 2004/0110135 A1 | 6/2004 | Nemetz et al. |
| 2008/0305961 A1 | 12/2008 | Abu Khabar |
| 2012/0141577 A1 | 6/2012 | Manthorpe et al. |

FOREIGN PATENT DOCUMENTS

| JP | H07-163388 | 6/1995 |
| JP | H07-509616 | 10/1995 |
| JP | 2001-503385 | 3/2001 |
| JP | 2002-539800 | 11/2002 |
| JP | 2002-540772 | 12/2002 |
| JP | 2003-189890 | 7/2003 |
| JP | 2004-141025 | 5/2004 |
| JP | 2010-511406 | 4/2010 |
| WO | 01/34815 | 5/2001 |
| WO | 2006/081831 | 8/2006 |

OTHER PUBLICATIONS

Rohrbaugh et al., Transcription unit of the rabbit betal globin gene; MCB, vol. 5, No. 1, 1985.*
Lanoix et al., EMBO J. vol. 7, No. 8, pp. 2515-2522, 1989.*
Gil et al., A sequence downstream of AAUAAA is required for rabbit beta-globin mRNA 3' end formation; Nature, vol. 312, pp. 473-474, 1984.*
International Search Report for PCT/JP2012/002936, mailed Jul. 24, 2012.

* cited by examiner

*Primary Examiner* — Addison D Ault
(74) *Attorney, Agent, or Firm* — Greenblum & Bernstein, P.L.C.

(57) ABSTRACT

Plasmid vectors have been widely used as a carrier of a DNA sequence capable of expressing a target RNA in cells. However, construction of these plasmid vectors requires technical skill and time. Thus, a quicker and easier method is required therefor. To solve this problem, a method using a linear DNA that has been amplified by the PCR method is examined. However, this method is disadvantageous in that RNA expression in cells is extremely low. Under these circumstances, the present inventors attempted to develop an RNA expression method using a linear DNA which can be produced mainly by using the PCR method alone and which enables a high level of RNA expression. As the results of intensive studies on terminator sequences to be used in a linear DNA, the present inventors found a smallest unit of a terminator sequence enabling linear DNA expression equivalent to that when using a plasmid vector. A linear DNA including the aforesaid terminator sequence can be produced quickly and easily, and enables RNA expression at a higher level. The present invention has been completed based on these findings.

7 Claims, 20 Drawing Sheets

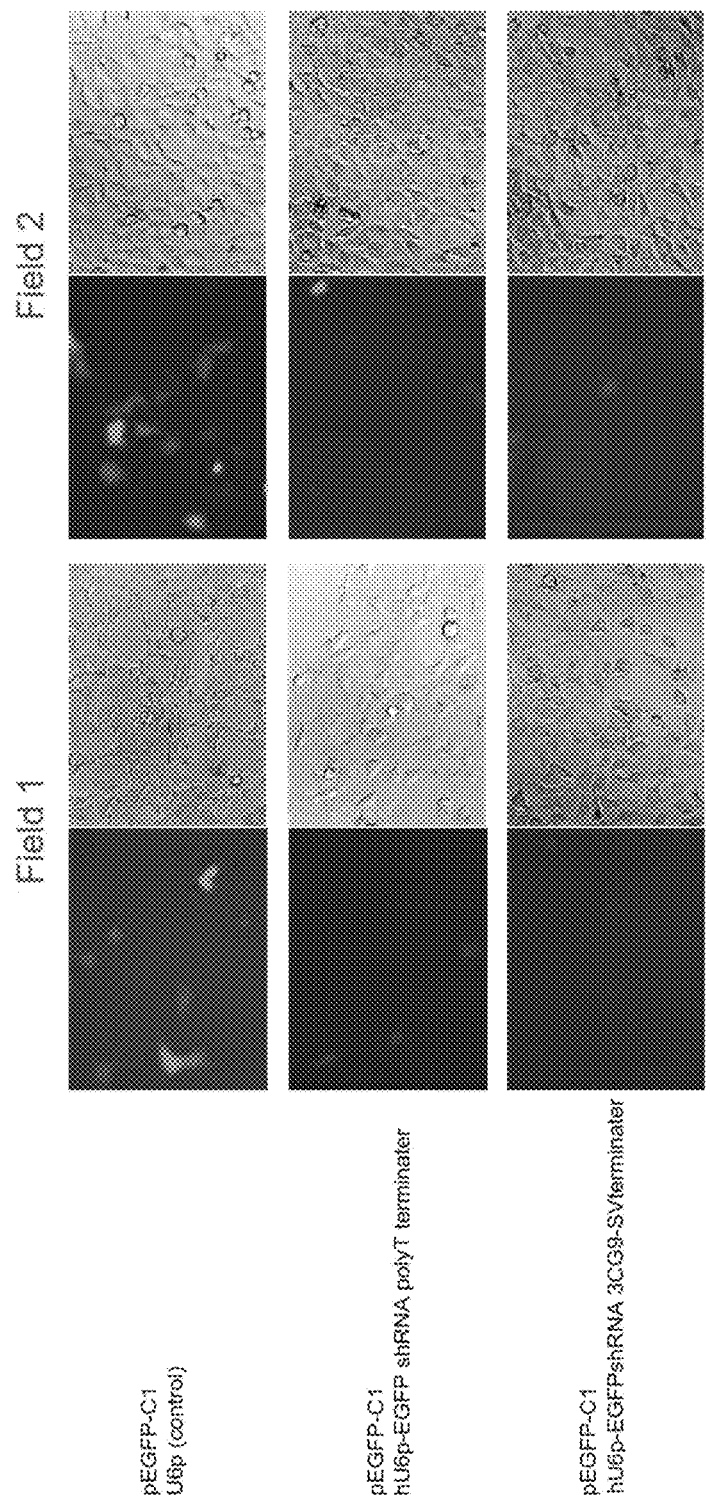

SEQUENCE LISTING

```
<160> NUMBER OF SEQ ID NOS: 58

<210> SEQ ID NO 1
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

<223> OTHER INFORMATION: beta-globin terminator 121-220

<400> SEQUENCE: 1
cttgagcatc tgacttctgg ctaataaagg aaatttattt tcattgcaat agtgtgttgg    60
aattttttgt gtctctcact cggaaggaca tatgggaggg                         100

<210> SEQ ID NO 2
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SV40 terminator 121-220

<400> SEQUENCE: 2
gcagcttata atggttacaa ataaagcaat agcatcacaa atttcacaaa taaagcattt    60
ttttcactgc attctagttg tggtttgtcc aaactcatca                         100

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      foward primer SV40 promoter (SV40p-441)

<400> SEQUENCE: 3
agacaataac cctgataaat gcttc                                          25

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      foward primer for CMV promoter (pEGFP-600)

<400> SEQUENCE: 4
gtaatcaatt acggggtcat ta                                             22

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      reverse primer for SV40 promoter (30c-SV40p-1c)

<400> SEQUENCE: 5
gatcagggca aacagaactt tgactcccat                                     30

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      reverse primer for CMV promoter (CMVpc)

<400> SEQUENCE: 6
ggtggcgacc ggtagcgcta gc                                             22

<210> SEQ ID NO 7

```
<211> LENGTH: 544
<212> TYPE: DNA
<213> ORGANISM: Oryctolagus cuniculus

<400> SEQUENCE: 7
actcctcagg tgcaggctgc ctatcagaag gtggtggctg gtgtggccaa tgccctggct    60
cacaaatacc actgagatct ttttccctct gccaaaaatt atggggacat catgaagccc   120
cttgagcatc tgacttctgg ctaataaagg aaatttattt tcattgcaat agtgtgttgg   180 aatttttgt gtctctcact cggaaggaca tatgggaggg caaatcattt aaaacatcag    240
aatgagtatt tggtttagag tttggcaaca tatgccatat gctggctgcc atgaacaaag   300
gtggctataa agaggtcatc agtatatgaa acagccccct gctgtccatt ccttattcca   360
tagaaaagcc ttgacttgag gttagatttt ttttatattt tgttttgtgt tattttttc    420 tttaacatcc ctaaaatttt ccttacatgt tttactagcc agattttttcc tcctctcctg   480 actactccca gtcatagctg tccctcttct cttatgaaga tccctcgacc tgcagcccaa   540
gctt                                                                544

<210> SEQ ID NO 8
<211> LENGTH: 230
<212> TYPE: DNA
<213> ORGANISM: Simian virus 40

<400> SEQUENCE: 8
ctgatcataa tcagccatac cacatttgta gaggttttac ttgctttaaa aaacctccca    60
cacctccccc tgaacctgaa acataaaatg aatgcaattg ttgttgttaa cttgtttatt   120
gcagcttata atggttacaa ataaagcaat agcatcacaa atttcacaaa taaagcattt   180
ttttcactgc attctagttg tggtttgtcc aaactcatca atgtatctta                230

<210> SEQ ID NO 9
<211> LENGTH: 225
<212> TYPE: DNA
<213> ORGANISM: Bos taurus

<400> SEQUENCE: 9
ctgtgccttc tagttgccag ccatctgttg tttgccccte ccccgtgcct tccttgaccc    60
tggaaggtgc cactcccact gtcctttcct aataaaatga ggaaattgca tcgcattgtc   120
tgagtaggtg tcattctatt ctgggggtg ggtggggca ggacagcaag ggggaggatt     180
gggaagacaa tagcaggcat gctggggatg cggtgggctc tatgg                   225

<210> SEQ ID NO 10
<211> LENGTH: 600
<212> TYPE: DNA
<213> ORGANISM: Cytomegalovirus

<400> SEQUENCE: 10
gtaatcaatt acggggtcat tagttcatag cccatatatg gagttccgcg ttacataact    60
tacggtaaat ggcccgcctg gctgaccgcc caacgacccc cgcccattga cgtcaataat   120
gacgtatgtt cccatagtaa cgccaatagg gactttccat tgacgtcaat gggtggagta   180
tttacggtaa actgcccact tggcagtaca tcaagtgtat catatgccaa gtacgccccc   240
tattgacgtc aatgacggta aatggcccgc ctggcattat gcccagtaca tgaccttatg   300
ggactttcct acttggcagt acatctacgt attagtcatc gctattacca tggtgatgcg   360
gttttggcag tacatcaatg ggcgtggata gcggtttgac tcacggggat ttccaagtct   420
```

```
ccacccatt gacgtcaatg ggagtttgtt ttggcaccaa aatcaacggg actttccaaa      480
atgtcgtaac aactccgccc cattgacgca aatgggcggt aggcgtgtac ggtgggaggt      540
ctatataagc agagctggtt tagtgaaccg tcagatccgc tagcgctacc ggtcgccacc      600
```

```
<210> SEQ ID NO 11
<211> LENGTH: 269
<212> TYPE: DNA
<213> ORGANISM: Simian virus 40

<400> SEQUENCE: 11
ggtgtggaaa gtccccaggc tccccagcag gcagaagtat gcaaagcatg catctcaatt      60
agtcagcaac caggtgtgga agtccccag gctcccagc aggcagaagt atgcaaagca      120
tgcatctcaa ttagtcagca accatagtcc cgcccctaac tccgcccatc cgcccctaa      180 ctccgcccag ttccgcccat tctccgcccc atggctgact aatttttttt atttatgcag      240
aggccgaggc cgcctcggcc tctgagcta                                         269
```

```
<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pCMV-Gluc+1160c

<400> SEQUENCE: 12
atcaagtttt ttggggtcga ggt                                              23
```

```
<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: beta-globin terminator 121-170

<400> SEQUENCE: 13
cttgagcatc tgacttctgg ctaataaagg aaatttattt tcattgcaat                 50
```

```
<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: beta-globin terminator 121-155

<400> SEQUENCE: 14
cttgagcatc tgacttctgg ctaataaagg aaatt                                 35
```

```
<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: beta-globin terminator 121-158

<400> SEQUENCE: 15
cttgagcatc tgacttctgg ctaataaagg aaatttat                                38

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: beta-globin terminator 121-161

<400> SEQUENCE: 16
cttgagcatc tgacttctgg ctaataaagg aaatttattt t                            41

<210> SEQ ID NO 17
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: beta-globin terminator 121-164

<400> SEQUENCE: 17
cttgagcatc tgacttctgg ctaataaagg aaatttattt tcat                         44

<210> SEQ ID NO 18
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: beta-globin terminator 121-167

<400> SEQUENCE: 18
cttgagcatc tgacttctgg ctaataaagg aaatttattt tcattgc                      47

<210> SEQ ID NO 19
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: bGlobinpA(121-140)c-hGluc+558c

<400> SEQUENCE: 19
ccagaagtca gatgctcaag ttagtcacca ccggcccccct tgatcttg                    48

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: bGlobinpA(121-149)c

<400> SEQUENCE: 20
```
ctttattagc cagaagtcag atgctcaag                                        29

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: bGlobinpA(121-152)c

<400> SEQUENCE: 21
ttcctttatt agccagaagt cagatgctca ag                                    32

<210> SEQ ID NO 22
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: bGlobinpA(121-155)c-hGluc+558c

<400> SEQUENCE: 22
aatttccttt attagccaga agtcagatgc tcaagttagt caccaccggc cccct           55

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: bGlobinpA(121-158)c

<400> SEQUENCE: 23
ataaatttcc tttattagcc agaagtcaga tgctcaag                              38

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: bGlobinpA(121-161)c

<400> SEQUENCE: 24
aaaataaatt tcctttatta gccagaagtc agatgctcaa g                          41

<210> SEQ ID NO 25
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: bGlobinpA(121-164)c

<400> SEQUENCE: 25
atgaaaataa atttccttta ttagccagaa gtcagatgct caag                       44

<210> SEQ ID NO 26

```
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: bGlobinpA(121-167)c

<400> SEQUENCE: 26
gcaatgaaaa taaatttcct ttattagcca gaagtcagat gctcaag                47

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: bGlobinpA(121-170)c

<400> SEQUENCE: 27
attgcaatga aataaatttc ctttattag ccagaagtca gatgctcaag              50

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: beta-globin terminator 121-160

<400> SEQUENCE: 28
cttgagcatc tgacttctgg ctaataaagg aaatttattt                        40

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: beta-globin terminator 121-180

<400> SEQUENCE: 29
cttgagcatc tgacttctgg ctaataaagg aaatttattt tcattgcaat agtgtgttgg  60

<210> SEQ ID NO 30
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: beta-globin terminator 121-190

<400> SEQUENCE: 30
cttgagcatc tgacttctgg ctaataaagg aaatttattt tcattgcaat agtgtgttgg  60
aattttttgt                                                        70

<210> SEQ ID NO 31
<211> LENGTH: 80
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: beta-globin terminator 121-200

<400> SEQUENCE: 31
cttgagcatc tgacttctgg ctaataaagg aaatttattt tcattgcaat agtgtgttgg      60 aatttttttgt gtctctcact                                                80

<210> SEQ ID NO 32
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: bglobinpA121-160-hGluc558taac

<400> SEQUENCE: 32
gaaaataaat tcctttatt agccagaagt cagatgctca agttagtcac caccggcccc      60
cttgatcttg                                                            70

<210> SEQ ID NO 33
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: bglobinpA121-180-hGluc558

<400> SEQUENCE: 33
taacttccaa cacactattg caatgaaaat aaatttcctt tattagccag aagtcagatg      60
ctcaagttag tcaccaccgg ccccctttgat cttg                                 94

<210> SEQ ID NO 34
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: bglobinpA121-190-hGluc558

<400> SEQUENCE: 34
taacacacaa aaattccaa cacactattg caatgaaaat aaatttcctt tattagccag       60
aagtcagatg ctcaagttag tcaccaccgg ccccctttgat cttg                     104

<210> SEQ ID NO 35
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: bglobinpA121-200c

<400> SEQUENCE: 35
agtgagagac acaaaaaatt ccaacacact attgcaatga aaataaattt cctttattag      60
```

```
ccagaagtca gatgctcaag                                              80

<210> SEQ ID NO 36
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: bglobinpA121-220c

<400> SEQUENCE: 36
ccctcccata tgtccttccg agtgagagac acaaaaaatt ccaacacact attgcaatga    60
aaataaattt cctttattag ccagaagtca gatgctcaag                          100

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SV40polyA+140c-Gluc+558c

<400> SEQUENCE: 37
ttgtaaccat tataagctgc ttagtcacca ccggcccct                           40

<210> SEQ ID NO 38
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SV40polyA(121-220)c

<400> SEQUENCE: 38
tgatgagttt ggacaaacca caactagaat gcagtgaaaa aaatgcttta tttgtgaaat    60
ttgtgatgct attgctttat ttgtaaccat tataagctgc                          100

<210> SEQ ID NO 39
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Am1+Am2

<400> SEQUENCE: 39
gcagcttata atggttacaa acgaagcaat agcatcacaa atttcacaaa cgaagcattt    60
ttttcactgc attctagttg tggtttgtcc aaactcatca                          100

<210> SEQ ID NO 40
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CMVp-27-hGluc+1
```

<400> SEQUENCE: 40
gatccgctag cgctaccggt cgccaccatg aagaccttaa ttcttgccg         49

<210> SEQ ID NO 41
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CMVp-27-hcluc

<400> SEQUENCE: 41
gatccgctag cgctaccggt cgccaccatg aagaccttaa ttcttgc           47

<210> SEQ ID NO 42
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: bGlobinpA 140c-hCluc+1662c

<400> SEQUENCE: 42
ccagaagtca gatgctcaag ctatttgcat tcatctggta ctt              43

<210> SEQ ID NO 43
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SV40polyA+140c-hCluc+ 1662c

<400> SEQUENCE: 43
ttgtaaccat tataagctgc ctatttgcat tcatctggta c                41

<210> SEQ ID NO 44
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SV40pA+140c-pEGFP+717cTAA

<400> SEQUENCE: 44
ttgtaaccat tataagctgc ttacttgtac agctcgtcca tgc              43

<210> SEQ ID NO 45
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: hGLuc+30c-SV40p-1c

<400> SEQUENCE: 45
gatcagggca aacagaactt tgactcccat gcgaaacgat cctcatcctg        50

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: hGLuc+1

<400> SEQUENCE: 46
atgggagtca aagttctgtt tgccc                                           25

<210> SEQ ID NO 47
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3CG9-hGluc+558c

<400> SEQUENCE: 47
cccgggccct tagtcaccac cggccccctt gatcttg                              37

<210> SEQ ID NO 48
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: bglobinpA(121-190)c-3CG9

<400> SEQUENCE: 48
acaaaaaatt ccaacacact attgcaatga aataaatttt cctttattag ccagaagtca     60
gatgctcaag cccgggccc                                                  79

<210> SEQ ID NO 49
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: bglobinpA(130-190)c-3CG9

<400> SEQUENCE: 49
acaaaaaatt ccaacacact attgcaatga aataaatttt cctttattag ccagaagtca     60
gcccgggccc                                                            70

<210> SEQ ID NO 50
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SV40pA(130-220)c-3CG9

<400> SEQUENCE: 50
tgatgagttt ggacaaacca caactagaat gcagtgaaaa aaatgcttta tttgtgaaat     60
ttgtgatgct attgctttat ttgtaaccat tcccgggccc          100

<210> SEQ ID NO 51
<211> LENGTH: 9
<212> TYPE: DNA
<213> ORGANISM: Artificial Sequence
<220> FEATURE:
<223> OTHER INFORMATION: Description of Artificial Sequence: Synthetic
      annealing sequence

<400> SEQUENCE: 51 gggcccggg          9

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SV40p-289(pCL-SV)

<400> SEQUENCE: 52
taccaccgat cgatcgctag ctgc          24

<210> SEQ ID NO 53
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SV40polyA+140c-hCluc+1662c

<400> SEQUENCE: 53
ttgtaaccat tataagctgc ctatttgcat tcatctggta c          41

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: hU6-223

<400> SEQUENCE: 54
gagggcctat ttcccatgat tcctt          25

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: hU6-1c

<400> SEQUENCE: 55
tgtttcgtcc tttccacaag atata          25

<210> SEQ ID NO 56
<211> LENGTH: 76
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: EGFPsiRNA-hU6-1c

<400> SEQUENCE: 56
aaaatacaac agccacaacg tctatctcga gatagacgtt gtggctgttg taccggtgtt    60
tcgtcctttc cacaag                                                    76

<210> SEQ ID NO 57
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3GC9-EGFPsiRNA-hU6-1c

<400> SEQUENCE: 57
gggcccggga aaatacaaca gccacaacgt ctatctcgag atagacgttg tggctgttgt    60
accggtgttt cgtcctttcc acaag                                          85

<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence: Synthetic
      consensus oligonucleotide
<220> FEATURE:
<221> NAME/KEY: modified_base
<222> LOCATION: (1)..(2)
<223> OTHER INFORMATION: a, c, t or g
<220> FEATURE:
<221> NAME/KEY: modified_base
<222> LOCATION: (9)..(10)
<223> OTHER INFORMATION: a, c, t or g
<220> FEATURE:
<221> NAME/KEY: modified_base
<222> LOCATION: (12)..(13)
<223> OTHER INFORMATION: a, c, t or g
<220> FEATURE:
<221> NAME/KEY: modified_base
<222> LOCATION: (15)..(15)
<223> OTHER INFORMATION: a, c, t or g

<400> SEQUENCE: 58
nnddtaaann vnnwn                                                     15
```

TERMINATOR SEQUENCE-CONTAINING REVERSE PRIMER FOR OVEREXPRESSION AND LINEAR DNA

SEQUENCE LISTING

The instant application contains a Sequence Listing which has been submitted electronically in ASCII format and is hereby incorporated by reference in its entirety. Said ASCII copy, created on Jan. 24, 2014, is named P44677_SL.txt and is 19,236 bytes in size.

FIELD OF THE INVENTION

The present invention relates to a reverse primer for RNA expression in mammalian cells and the like, the reverse primer being composed of a complementary sequence of a DNA sequence that includes a terminator sequence. The present invention also relates to a linear DNA for RNA expression in cells composed of a double-stranded DNA sequence that includes, in order, a promoter sequence, a target RNA-expressing DNA sequence, and a terminator sequence. The present invention also relates to a method for causing overexpression of RNA in cells by using the linear DNA.

BACKGROUND OF THE INVENTION

Technologies for causing expression of various proteins in cells are essential today, with function analysis of cells and proteins in cells, production of useful proteins, and the like in wide use. In order to cause expression of specific proteins within cells, a method of transfecting a gene into the cells is useful, and a method in which a plasmid vector is employed as a carrier of the gene to be transfected is widely used. A plasmid is a double-stranded, annular structure that exists within cytoplasm of a bacterium or yeast cell and autonomously performs replication independently of chromosomal DNA. In the field of genetic engineering, a plasmid that has undergone various modifications and had foreign genes inserted therein is transfected into a cell as a plasmid vector and is used in gene expression.

Many plasmid vectors primarily include replication origin points for replicating in a host cell of E. coli bacteria and the like; a promoter sequence; a terminator sequence (some also being referred to as a poly(A)-binding sequence or poly(A) sequence); a multicloning site that includes various restriction enzymes for inserting a drug resistant or auxotrophic marker gene or a foreign gene; and the like. The promoter sequence is a sequence controlling initiation of gene transcription. In many cases, sequences of approximately 500 to 1000 nucleobases are used. In order to be optimized for gene expression using a plasmid vector, these sequences often employ a promoter having a large amount of gene expression, such as a virus, or are modified from an original promoter sequence. Further, the terminator sequence is a sequence that controls termination of gene transcription, or that stabilizes transcribed RNA. In many cases, sequences of approximately 200 to 1000 nucleobases are used.

The simplest general example of a plasmid vector structure is as follows (FIG. 1): (1) a target RNA-expressing DNA sequence is amplified using a PCR method by employing a primer that includes a restriction enzyme site, then an amplified product of the target RNA-expressing DNA sequence is obtained that includes the restriction enzyme site on both ends thereof; (2) the amplified product obtained in step (1) and the plasmid vector are processed by the restriction enzyme; (3) a restriction enzyme processing product of step (2) is purified; (4) the plasmid vector and amplified product of step (3) are connected by a ligation reaction and rendered annular; (5) a ligation reaction product of step (4) undergoes transgenesis into E. coli bacteria, then is dispensed in a plate that includes a selected medical agent and is incubated overnight at 37° C.; (6) a colony of E. coli bacteria is taken from the plate of step (5), then the E. coli bacteria is cultivated in a liquid culture medium; (7) the plasmid vector is purified using the E. coli bacteria of step (6), then a sequence, structure, and the like of the resulting plasmid vector is confirmed; and (8) the E. coli bacteria having the target plasmid vector confirmed in step (7) are cultivated, then the plasmid vector is purified to obtain a necessary amount thereof. Typically, completing all of these steps requires five days to a week, or even longer. It can be said that the process is one of the experiments acting as a rate limit on a project's progress.

The plasmid vector is advantageous in that the plasmid vector is capable of maintaining comparative stability even when inside a transfected cultured cell, and of obtaining a high level of RNA expression. However, the structure of the plasmid vector requires a great deal of time for enzyme processing and growth of the E. coli bacteria, which requires time to complete, as noted above. Moreover, technical skill is required. Further, even the step of amplifying the constructed plasmid vector within the E. coli bacteria takes one night for the plasmid vector to undergo transgenesis into the E. coli bacteria and to form a colony. Culture of the E. coli bacteria that includes the plasmid vector takes from twelve hours to (typically) about one night, and amplification of the plasmid vector also takes time. Therefore, a method for gene expression is sought that is technically simple and greatly compresses the time required for construction and amplification of DNA for expression.

In recent years, due to the discovery of a polymerase with a high degree of accuracy, synthesis of genes in a few hours using a PCR method has become possible. Thus, instead of an annular plasmid vector that takes time and effort to produce, a method is considered in which a linear form of linear DNA amplified using the PCR method is transfected as-is into a cell to perform gene expression. When a gene for transfection produced with this method is capable of achieving sufficient gene expression within a cell, conventional plasmid construction requiring time and effort can be swapped for fast and easy production of linear DNA using the PCR method. The amount of time taken can thus be greatly compressed and development of a high level of through-put can be anticipated. However, there is a problem that even when the linear DNA produced by the PCR method undergoes gene transfer to a cell, an amount of expression is markedly lower as compared to a plasmid vector given the same genetic sequence, or expression does not occur.

Patent Literature 1 recites a method of preparing a DNA fragment using the PCR method, the DNA fragment including a promoter sequence, a target gene, an expression marker gene, a terminator sequence, and a polyadenylation signal sequence, which are sequences required for expression in cells. However, in order to resolve the problem that linear DNA is likely to degrade within the cell and that a high level of expression is difficult to obtain, the method of Patent Literature 1 adopts a technique of making the above-noted DNA fragment annular, and transfects an annular plasmid vector into the cells in a manner similar to conventional methods. Accordingly, time and effort required for making the DNA annular, selecting the DNA made annular, and the like is equivalent to the conventional time and effort, and is thus not capable of compressing the time and effort to any marked degree in comparison to conventional methods.

Patent Literature 2 teaches a linear DNA as a linear expression element, the linear DNA including a promoter, a coding region, and the like. A method described in Patent Literature 2 individually amplifies each structural element (such as the promoter), then, by annealing of single-stranded DNA overhanging terminals ends of each, the structural elements are non-covalently bonded together. In order to do this, a method using a dUMP-containing PCR primer and uracil-DNA glycosylase, a method using a non-basic phorphoramidate, a method using rU/RNaseA, and the like can be employed. However, there is a problem that all of the methods require high-cost reagents and cumbersome manipulation, and so they cannot be said to be methods for gene expression that enable application to high-throughput, that are technically simple, and that greatly compress time. Patent Literature 3 teaches a method for simple production of linear DNA fragments for gene expression in a cell-free system, the linear DNA fragments including a promoter and a terminator on a plasmid vector. However, Patent Literature 3 is unable to resolve the low level of gene expression using linear DNA in a cell culture.

Further, Non-patent Literature 1 teaches a method for expressing a plurality of genes, each having a different expression amount, using a single vector by including, on the same vector, a poly(A) signal of SV40 having a modified AATAAA sequence downstream of one target gene and including a poly(A) signal of SV40 not having the modified AATAAA sequence downstream of another target gene. In addition, Patent Literature 4 recites a method for amplifying protein production by modifying a nucleotide sequence of an untranslated region of DNA composed of an untranslated region that includes, in order, a coding region, a translation stop codon, and a polyadenylated signal, the nucleotide sequence being modified such that a distance between the translation stop codon and an AATAAA polyadenylated signal is 300 base pairs or less, then using the nucleotide sequence in a vector DNA. However, each of these methods makes use of an annular plasmid vector and increases the time and effort to produce the vector more than conventional methods. Accordingly, at present, no method has been discovered for gene expression using linear DNA that enables a high level of gene expression that rivals a plasmid vector in a cell culture, that is technically simple, and that greatly compresses the time required for production.

RELATED ART

Patent Literature

Patent Literature 1: Japanese Patent Laid-open Publication No. 2004-141025
Patent Literature 2: Japanese Publication of PCT International Application No. 2002-540772
Patent Literature 3: Japanese Patent Laid-open Publication No. 2003-189890
Patent Literature 4: Japanese Patent Laid-open Publication No. H7-163388

Non-Patent Literature

Non-patent Literature 1: Yuansheng Yang et al., Biotechnology and Bioengineering, 102, 1152-1160 (2008)

SUMMARY OF THE INVENTION

Problems to be Solved by the Invention

In order to handle a DNA sequence capable of expressing a target RNA in a cell, plasmid vectors are widely used as a carrier of the DNA sequence capable of expressing the target RNA. However, construction of the plasmid vectors requires technical skill as well as a great deal of time. Thus, a quicker and easier method is desired. To solve this problem, a method is examined in which a linear DNA that has been amplified by the PCR method is transfected into cells. However, among methods using linear DNA, this method is disadvantageous in that RNA expression in cells is extremely low in comparison to a case using the plasmid vectors. This method is thus not yet in practical use. An objective of the present invention is to provide a method for expressing RNA using a linear DNA which can be produced quickly and easily mainly by using the PCR method alone and which enables a high level of RNA expression rivaling cases where plasmid vectors are used.

Means for Solving the Problems

As a result of focusing on terminators to be used in a linear DNA and intensive studies of sequences thereof, the present inventors found a smallest unit terminator sequence in linear DNA enabling RNA expression equivalent to the expression when a plasmid vector is used. A linear DNA including the aforementioned terminator sequence can be easily and quickly constructed mainly with a PCR method and enables RNA expression at a higher level. The present invention has been completed based on these findings.

In other words, the present invention relates to: (1) a reverse primer for RNA expression in cells using linear DNA, the reverse primer being composed of a complementary sequence of a DNA sequence that includes a terminator sequence, and the terminator sequence being composed of between 30 and 200 nucleobases and including a sequence of nine connected nucleobases (A/T/G), (A/T/G), T, A, A, A, (A/T/G/C), (A/T/G/C), (A/G/C); (2) the reverse primer of (1) in which the complementary sequence of the DNA sequence that includes the terminator sequence is a complementary sequence of a DNA sequence that includes, in order, a specific sequence of a target RNA-expressing DNA sequence to be amplified and a terminator sequence; (3) the reverse primer of (1) in which the complementary sequence of the DNA sequence that includes the terminator sequence is a complementary sequence of a DNA sequence that includes, in order, an annealed sequence and a terminator sequence; (4) the reverse primer of any one of (1) to (3) above in which the terminator sequence is derived from a terminator sequence of β-globin or SV40 (simian virus 40); and (5) the reverse primer of any one of (1) to (4) above in which the terminator sequence is an entire length or a portion of a sequence shown in SEQ ID NO: 1 or SEQ ID NO: 2.

In addition, the present invention relates to: (6) a linear DNA for RNA expression in cells composed of a double-stranded DNA sequence that includes, in order, a promoter sequence, a target RNA-expressing DNA sequence, and a terminator sequence, the terminator sequence being composed of between 30 and 200 nucleobases and including a sequence of nine connected nucleobases (A/T/G), (A/T/G), T, A, A, A, (A/T/G/C), (A/T/G/C), (A/G/C); (7) the linear DNA of (6) in which an annealed sequence is provided between the target RNA-expressing DNA sequence and the terminator sequence; (8) the linear DNA of (6) or (7) above in which the terminator sequence is derived from a terminator sequence of β-globin or SV40 (simian virus 40); (9) the linear DNA of any one of (6) to (8) above in which the terminator sequence is an entire length or a portion of a sequence shown in SEQ ID NO: 1 or SEQ ID NO: 2; and (10) the linear DNA of any one of (6) to (9) in which the target RNA-expressing DNA sequence is a shRNA-expressing DNA sequence.

Moreover, the present invention relates to: (11) a method for RNA expression using a linear DNA having the linear DNA of (6) to (10) above transfected into a cell.

Effect of the Invention

The present invention enables production of a linear DNA capable of a high level of RNA expression in mammalian cells and the like and enables a high level of RNA expression in mammalian cells and the like by using the linear DNA. Further, appropriately selecting a sequence to be expressed enables not only protein overexpression, but also suppression of protein expression, and the like. An additional advantage of high versatility is also provided. According to the present invention, complex operations are rendered unnecessary due to chiefly employing the PCR method and a linear DNA can be produced quickly and easily. Therefore, a large amount of a sample can be handled at once, automation with machines becomes possible, and the present invention can also be effectively used in RNA expression experiments, screening, and the like using high through-put.

BRIEF DESCRIPTION OF THE DRAWINGS

FIG. 3 shows a method for producing linear DNA in one step of using a template where the target RNA-expressing DNA sequence is not connected downstream of the targeted promoter to bind a short terminator sequence of one hundred base pairs or fewer.

FIG. 4 shows a method for producing linear DNA in two steps of using the template where the target RNA-expressing DNA sequence is not connected downstream of the targeted promoter and binding a long terminator sequence of one hundred base pairs or more, or binding the terminator sequence using an annealed sequence.

FIG. 5 shows a method for producing linear DNA in which the template where the target RNA-expressing DNA sequence is not connected downstream of the targeted promoter is used to bind the target RNA-expressing DNA sequence using PCR.

FIG. 6 shows a different mode of the method for producing linear DNA in which the template where the target RNA-expressing DNA sequence is not connected downstream of the targeted promoter is used to bind the target RNA-expressing DNA sequence using PCR.

FIG. 7 is a graph measuring an amount of luciferase expression when a linear DNA (PCR amplified product) is transfected into COST cells, the linear DNA being composed of either a plasmid vector having a secreted luciferase gene inserted therein or a promoter of such a plasmid vector, a secreted luciferase gene, and a terminator sequence.

FIG. 9 shows results of measuring an amount of secreted luciferase gene expression for a case where graph numbers 1 to 12 from a left of the graph used, in order, a β-globin terminator sequence of nucleobase numbers 1 to 170, number 175, . . . and number 534, and for a case where graph numbers 13 to 24 from the left used, in order, a β-globin terminator sequence of nucleobase numbers 21 to 170, number 175, . . . and number 534. Graph numbers 25 to 108 from the left thereafter are similar. A nucleobase sequence of the β-globin terminator sequence of nucleobase numbers 121 to 170 (indicated by an asterisk) was obtained as a sequence capable of most efficiently achieving expression of the luciferase gene with the shortest sequence.

In FIG. 12, "121-155 (151T)" illustrates a variant terminator sequence having the nucleobase of nucleobase number 151 substituted with thymine (T) in the β-globin terminator sequence of nucleobase numbers 121 to 155, while "121-220 AATAAA mutation" illustrates a variant terminator sequence having AATAAA substituted with AAcgAA in the SV40 terminator sequence of nucleobase numbers 121 to 220. These are negative controls not provided with the sequence of nine connected nucleobases (A/T/G), (A/T/G), T, A, A, A, (A/T/G/C), (A/T/G/C), (A/G/C). "−" indicates a negative control using a linear DNA with no terminator sequence. "pCMV-Gluc" is a positive control using a plasmid vector. "CMV-Gluc linear" is a negative control using a linear DNA composed of a CMV promoter, a luciferase gene, and a pCMV-Gluc-derived terminator sequence. "3GC9" indicates a linear DNA (CMV-hGluc-3GC9) that includes, in order, a CMV promoter, a secreted luciferase gene, and an annealed sequence (GGGCCCGGG, SEQ ID NO: 51). All of "3GC9+121-190," "3GC9+130-190," and "3GC9+130-220" indicate a linear DNA having the annealed sequence (GGGCCCGGG, SEQ ID NO: 51) between the secreted luciferase gene and the terminator sequence.

In FIG. 13, "121-155 (151T)" illustrates a variant terminator sequence having the nucleobase of nucleobase number 151 substituted with thymine (T) in the β-globin terminator sequence of nucleobase numbers 121 to 155, while "121-220 AATAAA mutation" illustrates a variant terminator sequence having AATAAA substituted with AAcgAA in the SV40 terminator sequence of nucleobase numbers 121 to 220. These are negative controls not provided with the sequence of nine connected nucleobases (A/T/G), (A/T/G), T, A, A, A, (A/T/G/C), (A/T/G/C), (A/G/C). "−" indicates a negative control using a linear DNA with no terminator sequence. "pCMV-Gluc" is a positive control using a plasmid vector. "CMV-Gluc linear" is a negative control using a linear DNA composed of a CMV promoter, a luciferase gene, and a pCMV-Gluc-derived terminator sequence. "3GC9" indicates a linear DNA (CMV-hGluc-3GC9) that includes, in order, a CMV promoter, a secreted luciferase gene, and an annealed sequence (GGGCCCGGG, SEQ ID NO: 51). "3GC9+130-190" indicates a linear DNA having the annealed sequence (GGGCCCGGG, SEQ ID NO: 51) between the secreted luciferase gene and the SV40 terminator sequence.

In FIG. 14, "121-155 (151T)" illustrates a variant terminator sequence having the nucleobase of nucleobase number 151 substituted with thymine (T) in the β-globin terminator sequence of nucleobase numbers 121 to 155, while "121-220 AATAAA mutation" illustrates a variant terminator sequence having AATAAA substituted with AAcgAA in the SV40 terminator sequence of nucleobase numbers 121 to 220. These are negative controls not provided with the sequence of nine connected nucleobases (A/T/G), (A/T/G), T, A, A, A, (A/T/G/C), (A/T/G/C), (A/G/C). "−" indicates a negative control using a linear DNA with no terminator sequence. "pCMV-Gluc" is a positive control using a plasmid vector. "CMV-Gluc linear" is a negative control using a linear DNA composed of a CMV promoter, a luciferase gene, and a pCMV-Gluc-derived terminator sequence. "3GC9" indicates a linear DNA (CMV-hGluc-3GC9) that includes, in order, a CMV promoter, a secreted luciferase gene, and an annealed sequence (GGGCCCGGG, SEQ ID NO: 51). "3GC9+130-190" indicates a linear DNA having the annealed sequence (GGGCCCGGG, SEQ ID NO: 51) between the secreted luciferase gene and the SV40 terminator sequence.

In FIG. 15, "121-155 (151T)" illustrates a variant terminator sequence having the nucleobase of nucleobase number 151 substituted with thymine (T) in the β-globin terminator sequence of nucleobase numbers 121 to 155, while "121-220 AATAAA mutation" illustrates a variant terminator sequence having AATAAA substituted with AAcgAA in the SV40 terminator sequence of nucleobase numbers 121 to 220. These are negative controls not provided with the sequence of nine connected nucleobases (A/T/G), (A/T/G), T, A, A, A, (A/T/G/C), (A/T/G/C), (A/G/C). "−" indicates a negative control using a linear DNA with no terminator sequence. "pCMV-Gluc" is a positive control using a plasmid vector. "CMV-Gluc linear" is a negative control using a linear DNA composed of a CMV promoter, a luciferase gene, and a pCMV-Gluc-derived terminator sequence. "3GC9" indicates a linear DNA (CMV-hGluc-3GC9) that includes, in order, a CMV promoter, a secreted luciferase gene, and an annealed sequence (GGGCCCGGG, SEQ ID NO: 51). "3GC9+130-190" indicates a linear DNA having the annealed sequence (GGGCCCGGG, SEQ ID NO: 51) between the secreted luciferase gene and the SV40 terminator sequence.

In FIG. 16, "121-155 (151T)" illustrates a variant terminator sequence having the nucleobase of nucleobase number 151 substituted with thymine (T) in the β-globin terminator sequence of nucleobase numbers 121 to 155, while "121-220 AATAAA mutation" illustrates a variant terminator sequence having AATAAA substituted with AAcgAA in the SV40 terminator sequence of nucleobase numbers 121 to 220. These are negative controls not provided with the sequence of nine connected nucleobases (A/T/G), (A/T/G), T, A, A, A, (A/T/G/C), (A/T/G/C), (A/G/C). "–" indicates a negative control using a linear DNA with no terminator sequence. "pCMV-Gluc" is a positive control using a plasmid vector. "CMV-Gluc linear" is a negative control using a linear DNA composed of a CMV promoter, a luciferase gene, and a pCMV-Gluc-derived terminator sequence. "3GC9" indicates a linear DNA (CMV-hGluc-3GC9) that includes, in order, a CMV promoter, a secreted luciferase gene, and an annealed sequence (GGGCCCGGG, SEQ ID NO: 51). "3GC9+130-190" indicates a linear DNA having the annealed sequence (GGGCCCGGG, SEQ ID NO: 51) between the secreted luciferase gene and the SV40 terminator sequence.

FIG. 20 shows results of a case where the shRNA-expressing DNA sequence was used as the target RNA-expressing DNA sequence to be amplified. pEGFP-C1 and hU6p, or pEGFP-C1 and hU6p-EGFP shRNA poly-T terminator, or pEGFP-C1 and hU6p-EGFPshRNA 3GC9-SV terminator are transfected into HEK293 cells, then fluorescence after 48 hours was observed. In fields 1 and 2, a left side is fluorescence observation and a right side is a bright-field image.

MODE FOR CARRYING OUT THE INVENTION

Figure 1:
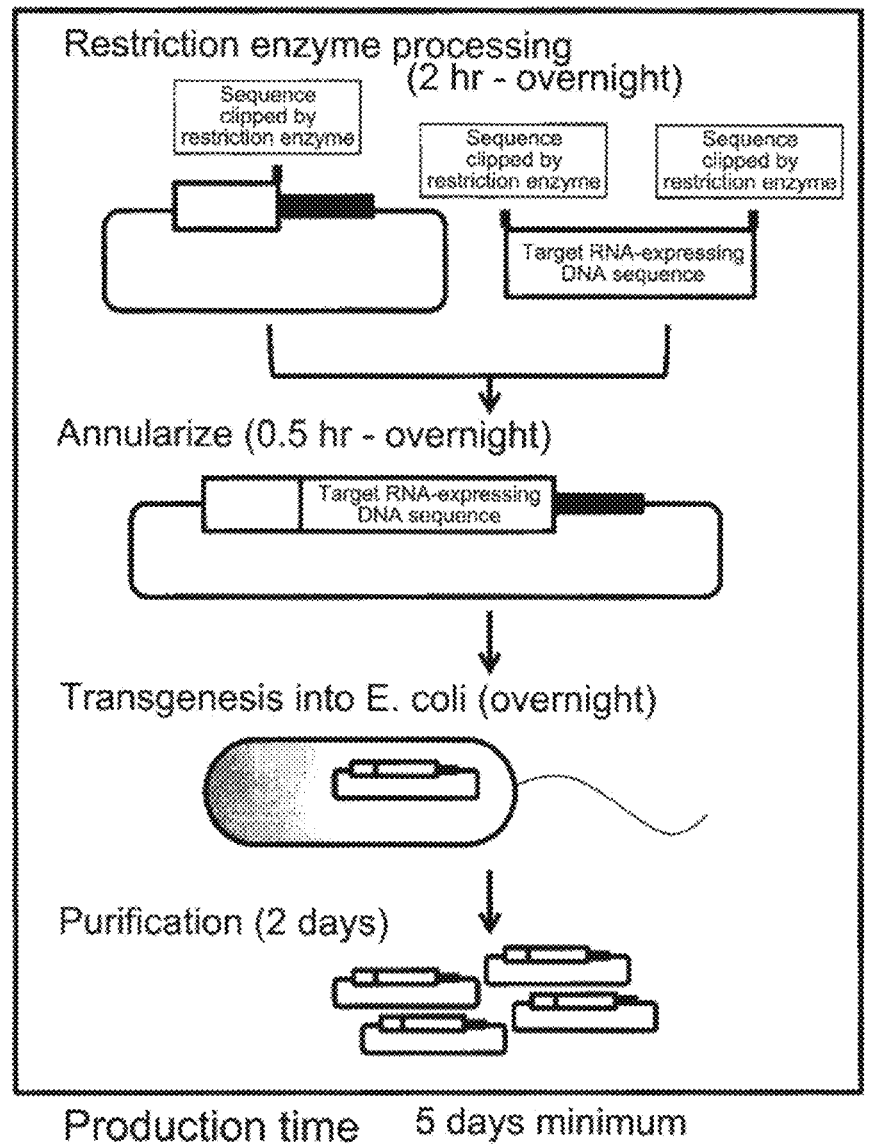
FIG. 1 shows an overview of a (conventional) method for producing a common plasmid.

A reverse primer according to the present invention is not particularly limited so long as the reverse primer is a reverse primer for RNA expression in cells that uses linear DNA and is composed of a complementary sequence of a DNA sequence that includes a terminator sequence, the terminator sequence being preferably composed of between 30 and 200 nucleobases, although the length of the terminator sequence is not particularly limited, and including a sequence of nine connected nucleobases (A/T/G), (A/T/G), T, A, A, A, (A/T/G/C), (A/T/G/C), (A/G/C) ((A/T/G), for example, meaning A, T, or G). The terminator sequence in the present invention may be derived from a DNA sequence at a transcription termination point and a vicinity thereof, the DNA sequence exhibiting transcription termination at a terminal end of a transcription unit. The terminator sequence in the present invention may also be derived from a prokaryotic terminator sequence, or from a eukaryotic terminator sequence. Examples of the prokaryotic terminator sequence can include a palindrome sequence (palindromic repeat sequence, inverted repeat nucleobase sequence) in which a transcribed sequence of RNA forms complementary double strands to create a hairpin structure, the palindrome sequence being composed of around a dozen nucleobases. Examples of the prokaryotic terminator sequence can also include sequences containing a T cluster, which is a contiguous sequence of thymine (T) serving as a transcription termination signal. Further, termination of transcription may be ρ factor-dependent termination in which a protein called ρ factor breaks down mRNA and base pairs of a template DNA to end transcription, or may be ρ factor-independent termination. Examples of the eukaryotic terminator sequence can include a polymerase terminator sequence that is any one of RNA polymerase I, II, and III, and can also include a 3' untranslated DNA sequence containing a polyadenylation signal (also called a poly(A) sequence or a poly(A)-binding sequence). The polyadenylation signal promotes binding of the poly(A) sequence to a 3' end of a primary transcript. The terminator sequence can be isolated from a bacterium, a fungus, a virus, an animal, a plant, and the like, and can also be artificially synthesized based on a sequence in a database.

The terminator sequence of the present invention can be selected as appropriate depending on a type of cell in which RNA expression is to occur, a type of promoter, a type of target RNA-expressing DNA sequence, and the like. Herein, a "target RNA-expressing DNA sequence" refers to a DNA sequence which is likely to express a targeted RNA. Examples of a source of the terminator sequence can include a β-globin terminator sequence, an SV40 terminator sequence, a BGH (bovine growth hormone) terminator sequence, an HSV-TK terminator sequence, a CYC1 terminator sequence, an ADH terminator sequence, a SPA terminator sequence, an Agrobacterium tumefaciens nopaline syntase (NOS) gene terminator sequence, a cauliflower mosaic virus (CaMV) 35S gene terminator sequence, a maize-derived Zein gene terminator sequence, a rubisco small subunit (SSU) gene terminator sequence, a subterranean clover stunt virus (SCSV) gene terminator sequence, or a LacZ alpha terminator sequence, poly-T terminator sequence, and the like. Preferable examples can include a rabbit β-globin terminator sequence (SEQ ID NO: 7), the SV40 terminator sequence (SEQ ID NO: 8), and the BGH (bovine growth hormone) terminator sequence (SEQ ID NO: 9). More preferable examples can include the β-globin terminator sequence (SEQ ID NO: 7) or the SV40 terminator sequence (SEQ ID NO: 8).

The terminator sequence of the present invention that includes the sequence of nine connected nucleobases (A/T/G), (A/T/G), T, A, A, A, (A/T/G/C), (A/T/G/C), (A/G/C) (also referred to as "the terminator sequence of the present invention" hereafter) may be a terminator sequence that includes a sequence of nine connected nucleobases in which a first nucleobase is A (adenine), T (thymine), or G (guanine); a second nucleobase is A, T, or G; a third nucleobase is T; a fourth nucleobase is A; a fifth nucleobase is A; a sixth nucleobase is A; a seventh nucleobase is A, T, G, or C (cytosine); an eighth nucleobase is A, T, G, or C; and a ninth nucleobase is A, G, or C. The terminator sequence of the present invention may include one, two, or more of the aforementioned nine connected nucleobases. A length of the above-noted terminator sequence that includes the nine connected nucleobases (A/T/G), (A/T/G), T, A, A, A, (A/T/G/C), (A/T/G/C), (A/G/C) is preferably short, from a viewpoint of reducing time and effort required to construct a double-stranded linear DNA for RNA expression. However, the length can be adjusted as appropriate depending on a level of RNA expression in desired cells. A length of the terminator sequence in a reverse primer or a linear DNA according to the present invention is not particularly limited. However, examples of the length can preferably include between 30 and 200 nucleobases, preferably between 35 and 150 nucleobases, and more preferably between 40 and 100 nucleobases. Most preferably, an example can be given of a sequence having a length of between 35 and 100 nucleobases that most notably includes the nine connected nucleobases (A/T/G), (A/T/G), T, A, A, A, (A/T/G/C), (A/T/G/C), (A/G/C) within a portion or an entire length of a nucleobase sequence (SEQ ID NO: 1 or 2) of nucleobase numbers 121 to 220 in the nucleobase sequence of the terminator sequence of the β-globin shown in SEQ ID NO: 7 or the SV40 shown in SEQ ID NO: 8. Examples of such a sequence can include a nucleobase sequence in the β-globin terminator sequence shown in SEQ ID NO: 7, shown by nucleobase numbers 121 to 220 (SEQ ID NO: 1), nucleobase numbers 121 to 200 (SEQ ID NO: 31), nucleobase numbers 121 to 190 (SEQ ID NO: 30), nucleobase numbers 121 to 180 (SEQ ID NO: 29), nucleobase numbers 121 to 170 (SEQ ID NO: 13), nucleobase numbers 121 to 167 (SEQ ID NO: 18), nucleobase numbers 121 to 164 (SEQ ID NO: 17), nucleobase numbers 121 to 161 (SEQ ID NO: 16), nucleobase numbers 121 to 160 (SEQ ID NO: 28), nucleobase numbers 121 to 158 (SEQ ID NO: 15), and nucleobase numbers 121 to 155 (SEQ ID NO: 14). Examples of such a sequence can also include a nucleobase sequence in the SV40 terminator sequence shown in SEQ ID NO: 8, shown by nucleobase numbers 121 to 220 (SEQ ID NO: 2). In the present disclosure, "terminator sequence" may in some cases refer not only to the DNA sequence but also to the DNA itself.

Examples of the cell in which RNA expression is to occur in the present invention can include a mammalian cell, a plant cell, an insect cell, E. coli bacteria, yeast, and the like. Of these, mammalian cells are preferable, examples of which can include cells derived from humans, monkeys, mice, rats, hamsters, rabbits, goats, sheep, horses, pigs, dogs, and the like. Of these, preferable examples are cells derived from humans and mice. Examples of a cell line in which RNA expression is to occur in the present invention include 293 cells, NIH-3T3 cells, HeLa cells, COST cells, HOS cells, SaM-1 cells, jurkat cells, MCF-7 cells, HepG2 cells, CaCO-2 cells, SaOS cells, K562 cells, CV-1 cells, COS-1 cells, L929 cells, F9 cells, MC-3T3-E1 cells, PC-12 cells, ROS17/2.8 cells, CHO-K1 cells, BHK-21 cells, and the like. The cell line may also be ES cells of EB3 cells and the like, primary cell cultures harvested from tissue, and the like.

The reverse primer of the present invention is not particularly limited; however, examples can include a reverse primer having thirty nucleobases or more, preferably between 30 and 200 nucleobases, more preferably between 35 and 150 nucleobases, and even more preferably between 40 and 100 nucleobases. The reverse primer of the present invention can be produced by, for example, performing artificial chemical synthesis, amplifying a DNA sequence of the reverse primer onto a template with a PCR method, amplifying a plasmid in which the DNA sequence of the reverse primer is incorporated, the amplification performed using E. coli bacteria and the like, then snipping using a restriction enzyme and the like. The reverse primer of the present invention may also be obtained commercially. To an extent that a PCR reaction is not inhibited, the reverse primer and a forward primer of the present invention may be a DNA molecule which has been labeled or modified by a labeled molecule, a tag, an isotope, and the like. Examples of such a labeled molecule can include a fluorophore, a chemical substance, and the like, while examples of the tag can include a HA tag, FLAG tag, MYC tag, GFP tag, MBP tag, GST tag, HIS tag, and the like.

In the reverse primer of the present invention, a complementary sequence of a DNA sequence containing a terminator sequence can be treated as a complementary sequence of a DNA sequence that includes, in order, a specific sequence of the target RNA-expressing DNA sequence to be amplified and a terminator sequence. Examples of the target RNA-expressing DNA sequence to be amplified in the present invention include a DNA sequence coding a target gene and a DNA sequence expressing a target functional nucleic acid, such as an shRNA (small hairpin RNA)-expressing sequence, an siRNA (short interfering RNA)-expressing sequence, an miRNA (micro-RNA), a nucleic acid aptamer-expressing sequence, a decoy-expressing sequence, an antisense oligonucleotide-expressing sequence, and a ribozyme-expressing sequence. In a case where expression of a protein is targeted, a DNA sequence coding for a gene can be defined and may be composed of a DNA sequence for expressing the protein. An entire length of the sequence coding for the gene or a portion thereof is acceptable, and a variant is also acceptable. Further, a source thereof may be a gene isolated from any organism, and may be an artificial gene produced through genetic engineering. A start codon on an N-terminus and a stop codon on a C-terminus in a gene may also be included or not, as appropriate. In addition, in a case where protein expression knock-down is targeted, an shRNA-expressing DNA sequence, an siRNA-expressing DNA sequence, or an antisense oligonucleotide can be defined as the target RNA-expressing DNA sequence to be amplified. In a case where a protein activation effect is inhibited or suppressed, a nucleic acid aptamer-expressing sequence or a ribozyme-expressing sequence can be defined as the target RNA-expressing DNA sequence to be amplified. In a case where transcription of a specific gene is suppressed, a decoy-expressing sequence can be defined as the target RNA-expressing DNA sequence to be amplified.

In addition, in the reverse primer of the present invention, a complementary sequence of a DNA sequence having a terminator sequence can be treated as a complementary sequence of a DNA sequence that includes, in order, an annealed sequence and a terminator sequence. The annealed sequence may be a sequence enabling a primer and a template to be annealed according to the aforementioned sequence and a PCR reaction to occur. Examples of the annealed sequence can include a nucleobase sequence of, preferably, between 5 and 20 nucleobases, more preferably between 7 and 15 nucleobases, and even more preferably between 8 and 12 nucleobases. The nucleobase sequence of the annealed sequence is also not particularly limited. From a viewpoint of annealing the primer efficiently and with a short sequence, a ratio of guanine (G) or cytosine (C) in the annealed sequence is preferably 50% or more, is more preferably 60% or more, and is even more preferably 70% or more. A favorable example can be given of nine nucleobases GGGCCCGGG (SEQ ID NO: 51) with a GC rate of 100%. In the present disclosure, the annealed sequence may in some cases refer not only to the DNA sequence but also to the DNA itself.

A linear DNA according to the present invention is not particularly limited so long as the linear DNA is a double-stranded DNA for RNA expression in cells such as mammalian cells that includes, in order, a promoter sequence, a target RNA-expressing DNA sequence, and a terminator sequence, the terminator sequence being preferably composed of between 30 and 300 nucleobases, although the length of the terminator sequence is not particularly limited, and including the sequence of nine connected nucleobases (A/T/G), (A/T/G), T, A, A, A, (A/T/G/C), (A/T/G/C), (A/G/C). The terminator sequence is preferably derived from a β-globin, SV40, or BGH terminator sequence, and of these, a sequence for a portion or an entire length of a sequence shown in SEQ ID NOS: 1 or 2 is particularly preferred. Further, the linear DNA of the present invention may include any component other than the promoter sequence, the target RNA-expressing DNA sequence, and the terminator sequence. The linear DNA of the present invention may be a linear DNA that further includes a sequence such as an enhancer enhancing promoter activity, a tag, and the like; an annealed sequence; and the like. When an annealed sequence is included, the annealed sequence can be provided between the target RNA-expressing DNA sequence and the terminator sequence; between the promoter sequence and the target RNA-expressing DNA sequence; and in two locations, between the target RNA-expressing DNA sequence and the terminator sequence as well as between the promoter sequence and the target RNA-expressing DNA sequence. In addition, the linear DNA of the present invention may be artificially synthesized, so long as it is DNA in a linear shape. The linear DNA of the present invention can be produced using the reverse primer of the present invention and, to an extent that does not inhibit transcription of mRNA, may be modified (e.g., methylated, glycosylated, and the like). The linear DNA of the present invention is preferably double-stranded DNA.

Examples of the target RNA-expressing DNA sequence to be amplified in the linear DNA of the present invention include a DNA sequence coding a gene and a DNA sequence expressing a functional nucleic acid, such as a shRNA (small hairpin RNA)-expressing sequence, a siRNA (short interfering RNA)-expressing sequence, a miRNA (micro-RNA), a nucleic acid aptamer-expressing sequence, a decoy-expressing sequence, an antisense oligonucleotide-expressing sequence, and a ribozyme-expressing sequence. In a case where expression of a protein is targeted, a DNA sequence coding for a gene can be defined and may be composed of a DNA sequence for expressing the protein. An entire length of the sequence coding for the gene or a portion thereof is acceptable, and a variant is also acceptable. Further, a source thereof may be a gene isolated from any organism, and may be an artificial gene produced through genetic engineering. A start codon on an N-terminus and a stop codon on a C-terminus in a gene may also be included or not, as appropriate. In addition, in a case where protein expression knock-down is targeted, the target RNA-expressing DNA sequence to be amplified can be defined as a shRNA-expressing DNA sequence, a siRNA-expressing DNA sequence, or an antisense oligonucleotide. In a case where a protein activation effect is inhibited or suppressed, a nucleic acid aptamer-expressing sequence or a ribozyme-expressing sequence can be defined as the target RNA-expressing DNA sequence to be amplified. In a case where transcription of a specific gene is suppressed, a decoy-expressing sequence can be defined as the target RNA-expressing DNA sequence to be amplified.

Application of the linear DNA of the present invention is not particularly limited. However, the linear DNA of the present invention can be used as a DNA vaccine, for example, by treating as the target RNA-expressing DNA sequence to be amplified a sequence expressing a protein having a therapeutic effect on a disorder or a sequence having an inhibitory function on expression of a protein involved in causing or advancing a disorder. In addition, the linear DNA of the present invention can also bind sequences inhibiting degradation within an organism (e.g., binding telomeric structures) to the N-terminus and the C-terminus. In addition, the N-terminus and C-terminus can be connected to create an annular form by a restriction enzyme recognition sequence binding blunt ends of the N-terminus and the C-terminus together or binding the N-terminus and C-terminus to the N-terminus and C-terminus, or by a sequence capable of complementary bonding in which the N-terminus and C-terminus are bound as appropriate.

A promoter in the linear DNA of the present invention can be selected as appropriate by a type of cell, such as mammalian cells, expressing the linear DNA, or by the target RNA-expressing DNA sequence, the terminator sequence, and the like. Examples of the aforementioned cells can include mammalian cells, plant cells, insect cells, $E.\ coli$ bacteria, and yeast. A promoter capable of inducing RNA expression in, of the above, mammalian cells is preferable. Examples of the promoter can include a human cytomegalovirus (CMV) promoter, a simian virus (SV40) promoter, a late-stage adenovirus (Adenovirus Major Late, or AML) AML promoter, an SR-α promoter which is a promoter of fusion of SV40 and HTLV-1 LTR, a human elongation factor 1-alpha (EF1-α) promoter, a human ubiquitin C promoter, an α-actin promoter, a β-actin promoter, a U6 promoter, an H1 promoter, a Tet-Off promoter in which RNA expression is suppressed by tetracycline, a Tet-On promoter in which RNA expression is induced by tetracycline, a metallothionein promoter in which inducement is by a metal such as zinc or various stimuli, and an ARE promoter in which inducement is by active oxygen. Of these, a preferred example can be given of the human cytomegalovirus (CMV) promoter (SEQ ID NO: 10) and the simian virus (SV40) promoter (SEQ ID NO: 11). To an extent that the promoter is likely to have a function in inducing RNA expression, the promoter may be a partial sequence thereof, and may include substitution, deletion, and insertion of DNA sequences.

The linear DNA of the present invention may be produced using chemical synthesis or genetic engineering methods. Specifically, preferred examples can be given of a method in which synthesis is performed using a DNA synthesizing apparatus; a method in which a linear DNA sequence is inserted into a plasmid vector and the vector is amplified using $E.\ coli$ bacteria; and a method using the PCR method. The method of producing the linear DNA of the present invention using the PCR method can be adjusted for production as appropriate according to a template, a length of a terminator sequence, and the like. The template used in the method of producing the linear DNA of the present invention using the PCR method can use DNA in which the target RNA-expressing DNA sequence is already movably connected downstream of the targeted promoter, and can employ DNA where the target RNA-expressing DNA sequence is not movably connected downstream of the targeted promoter.

The template in which the target RNA-expressing DNA sequence is already connected downstream of the targeted promoter is DNA that includes, in order, the promoter sequence and the target RNA-expressing DNA sequence, and may be DNA having the target RNA-expressing DNA sequence movably connected downstream of the targeted promoter, and may be a double-stranded linear form of DNA or an annular form of DNA. Further, other genes or other components such as a replication origin point may be included in the same DNA, and a preferred example can be given of a stable *E. coli* bacteria plasmid that is capable of readily amplifying using *E. coli* bacteria. In addition, in a case where no DNA is present having the target RNA-expressing DNA sequence already connected downstream of the targeted promoter, the target RNA-expressing DNA sequence can be movably connected downstream of the targeted promoter by a PCR reaction. The template used in such a case may be a double-stranded linear form of DNA or an annular form of DNA, and sequences of the promoter and the target RNA-expressing DNA sequence, respectively, may be on different, independent DNA molecules, or may be on the same DNA molecule. In addition, the other genes or other components such as the replication origin point may be included in the same DNA as the promoter and the target RNA-expressing DNA sequence, which is the template. Moreover, in a case where no target RNA-expressing DNA sequence is present downstream of the targeted promoter, the target RNA-expressing DNA sequence can also be connected downstream of the targeted promoter using the PCR reaction by defining a complementary sequence of the target RNA-expressing DNA sequence on the primer.

The method of producing the linear DNA of the present invention using the PCR method can be separated into two types according to the length of the terminator sequence to be used. When producing the linear DNA of the present invention using the PCR method, the terminator sequence can bind to a linear form of DNA using one PCR reaction when the terminator sequence to be used is short, and the terminator sequence can bind to a linear form of DNA using two or more PCR reactions when the terminator sequence to be used is long. Herein, a "short terminator sequence" has a length in which the terminator sequence can be engineered within one primer and refers to a length capable of binding the terminator sequence to a linear form of DNA using one PCR reaction. A "short terminator sequence" refers to less than one hundred nucleobases. Herein, a "long terminator sequence" has a length in which the terminator sequence cannot be engineered within a primer and refers to a length in which a linear form of DNA binding the terminator sequence can be produced using two or more PCR reactions. A "long terminator sequence" can have, as a guideline, more than one hundred nucleobases. The terminator sequence in the linear DNA of the present invention can be used with a length of two hundred or fewer nucleobases, which is shorter than that of a conventionally-used terminator sequence. Therefore, a favorable example can be given of a method in which two PCR reactions are performed in production of a linear DNA having a long terminator sequence. Further, in a case where the annealed sequence is used and a short terminator sequence is connected to the target RNA-expressing DNA sequence, one PCR reaction can be performed in order to bind the annealed sequence to the target RNA-expressing DNA sequence. Moreover, one PCR reaction can be performed in order to connect the short terminator sequence to the DNA that includes, in order, the target RNA-expressing DNA sequence and the annealed sequence. In a case where the annealed sequence is used and a long terminator sequence is connected to the target RNA-expressing DNA sequence, one PCR reaction can be performed in order to bind the annealed sequence to the target RNA-expressing DNA sequence. Moreover, two PCR sequences can be performed in order to connect the long terminator sequence to the DNA that includes, in order, the target RNA-expressing DNA sequence and the annealed sequence.

The forward primer and reverse primer used in production of the linear DNA of the present invention, which are composed of sequences specific to the promoter, may be primers composed of sequences specific to the promoter and can include primers preferably having between 15 and 50 nucleobases, more preferably having between 16 and 40 nucleobases, and even more preferably having between 17 and 30 nucleobases. The forward primer and reverse primer can also be artificially chemically synthesized and can be obtained commercially. Examples of a primer amplifying the CMV promoter and SV40 promoter DNA can include SEQ ID NOS: 4 and 6, or SEQ ID NOS: 3 and 5. In addition, the forward primer and reverse primer composed of specific sequences of the target RNA-expressing DNA sequence to be amplified may be primers composed of specific sequences of the target RNA-expressing DNA sequence to be amplified and can include primers preferably having between 15 and 50 nucleobases, more preferably having between 16 and 40 nucleobases, and even more preferably having between 17 and 30 nucleobases. The forward primer and reverse primer can also be artificially chemically synthesized and can be obtained commercially.

When producing the linear DNA of the present invention using the PCR method, the PCR method can be performed by a routine method. Composition of a reaction solution, reaction temperature, reaction time, and the like can be adjusted as appropriate according to an amount of amplified product or the like required by the template or the primer. In a case where a PCR reaction consisting of a plurality of steps is performed and a PCR product from an earlier step is used as the template, purification can be performed using agarose gel electrophoresis, a spin column, and the like. However, to an extent that the PCR reaction is not inhibited, the PCR product from the earlier step may be employed as the template of a different step without purifying a portion of the reaction solution.

Hereafter, a method of producing the linear DNA of the present invention using the PCR method is illustrated by examples.

Figure 2:
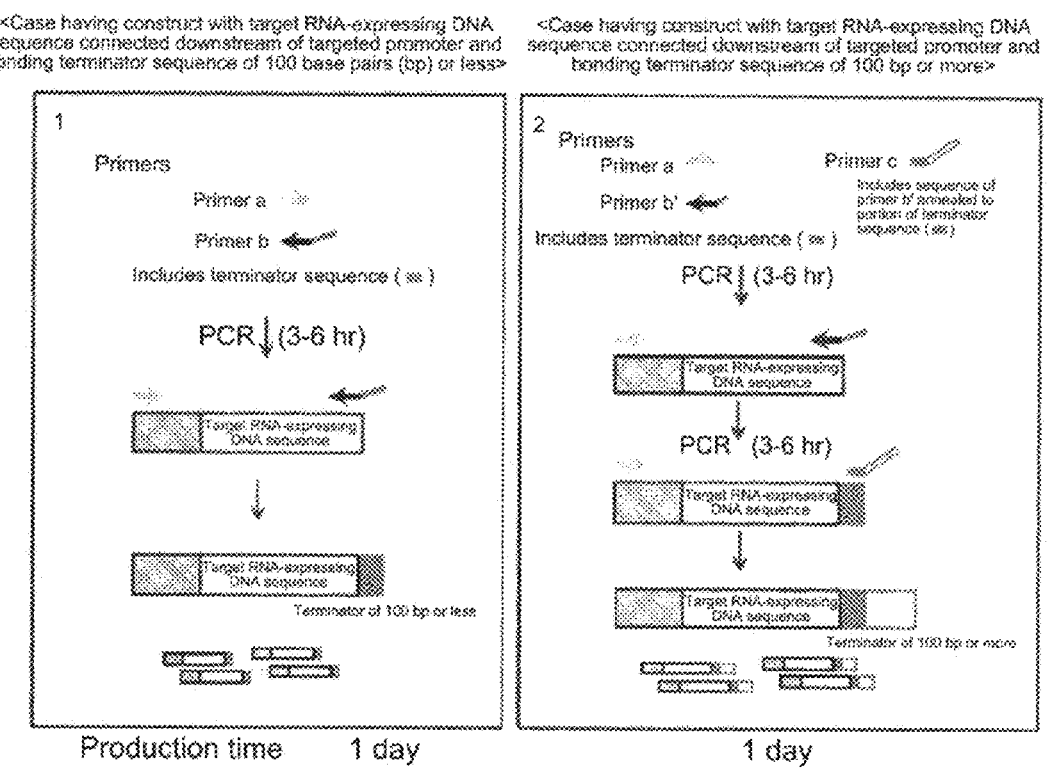
FIG. 2 shows overviews 1 and 2 of a method for producing linear DNA in the present invention. Overview 1 (left panel) shows a method for producing linear DNA in one step in a case where a template having a target RNA-expressing DNA sequence connected downstream of a targeted promoter is used to bind a short terminator sequence of one hundred base pairs or fewer. Overview 2 (right panel) shows a method for producing linear DNA in two steps of using the template having the target RNA-expressing DNA sequence connected downstream of the targeted promoter to bind a long terminator sequence of one hundred base pairs or more, or to bind a terminator sequence using an annealed sequence.

1. Case when DNA that includes, in order, a promoter sequence and a target RNA-expressing DNA sequence is used as a template and the terminator sequence is bound in one step (FIG. 2, left panel):

In a case where DNA is present having the target RNA-expressing DNA sequence already connected downstream of the targeted promoter, the linear DNA according to the present invention can be produced using a PCR reaction employing primers according to (a) and (b) below.

(a) Forward primer specific to promoter sequence (a forward primer for amplification of a promoter sequence composed of a specific sequence in the promoter);

(b) Reverse primer composed of a complementary sequence of a DNA sequence that includes, in order, a specific sequence of the target RNA-expressing DNA sequence to be amplified and a terminator sequence, the terminator sequence being composed of between 30 and 200 nucleobases and including a sequence of nine connected nucleobases (A/T/G), (A/T/G), T, A, A, A, (A/T/G/C), (A/T/G/C), (A/G/C);

In addition, the primers of (a) and (b) can be provided as a kit for producing a double-stranded linear DNA for RNA expression in mammalian cells and the like. Such a kit may also include, in addition to the aforementioned primers, a buffer, dNTPs, a template for a control, and the like.

2. Case when DNA that includes, in order, a promoter sequence and a target RNA-expressing DNA sequence is used as a template and the terminator sequence is bound in two steps (FIG. 2, right panel):

In a case where a construct is present having the target RNA-expressing DNA sequence already connected downstream of the targeted promoter, the linear DNA according to the present invention can be produced using the PCR reaction comprising steps 1 and 2 below.

<Step 1>

DNA that includes, in order, a promoter sequence and a target RNA-expressing DNA sequence is used as a template and primers according to (a) and (b') below are employed to produce, with the PCR method, DNA composed of a sequence that includes, in order, a promoter sequence, a target RNA-expressing DNA sequence, and a portion of the terminator sequence.

(a) Forward primer specific to promoter sequence;

(b') Reverse primer composed of a complementary sequence of a DNA sequence that includes, in order, a specific sequence of the target RNA-expressing DNA sequence to be amplified and the terminator sequence;

<Step 2>

With an amplified product obtained in step 1 as the template, primers according to (a) and (c) below can be employed to amplify, with the PCR method, DNA that includes, in order, the promoter sequence, the target RNA-expressing DNA sequence, and the terminator sequence, and to produce the linear DNA according to the present invention.

(a) Forward primer specific to promoter sequence;

(c) Reverse primer composed of complementary sequence of terminator sequence;

The reverse primer of (b') need not include the sequence of nine connected nucleobases (A/T/G), (A/T/G), T, A, A, A, (A/T/G/C), (A/T/G/C), (A/G/C) in the terminator sequence. Instead, it is sufficient for the terminator sequence to include the sequence of nine connected nucleobases (A/T/G), (A/T/G), T, A, A, A, (A/T/G/C), (A/T/G/C), (A/G/C) in the linear DNA of the present invention, which includes, in order, the promoter sequence, the target RNA-expressing DNA sequence, and the terminator sequence, the linear DNA being amplified by the PCR reaction of step 2. An example can be given in which the linear DNA of the present invention is, for example, produced not by including the sequence of nine connected nucleobases (A/T/G), (A/T/G), T, A, A, A, (A/T/G/C), (A/T/G/C), (A/G/C) in the reverse primer of (b'), but is instead produced by the reverse primer of (c) including the sequence of nine connected nucleobases. In addition, the primers of (a), (b'), and (c) can be provided as a kit for producing a double-stranded linear DNA for RNA expression in mammalian cells and the like. Such a kit may also include, in addition to the aforementioned primers, a buffer, dNTPs, a template for a control, and the like.

As a different mode, the linear DNA of the present invention can be produced by the PCR reaction according to steps 1 and 2, below, using an annealed sequence.

<Step 1>

DNA that includes, in order, a promoter sequence and a target RNA-expressing DNA sequence is used as a template and primers according to (a) and (f) below are employed to produce, with the PCR method, DNA composed of a sequence that includes, in order, a promoter sequence, a target RNA-expressing DNA sequence, and an annealed sequence.

(a) Forward primer specific to promoter sequence;

(f) Reverse primer composed of a complementary sequence of a DNA sequence that includes, in order, a specific sequence of the target RNA-expressing DNA sequence to be amplified and the annealed sequence;

<Step 2>

With an amplified product obtained in step 1 as the template, primers according to (a) and (c') below can be employed to amplify, with the PCR method, DNA that includes, in order, the promoter sequence, the target RNA-expressing DNA sequence, the annealed sequence, and the terminator sequence, and to produce the linear DNA according to the present invention.

(a) Forward primer specific to promoter sequence;

(c') Reverse primer composed of a complementary sequence of a DNA sequence that includes, in order, an annealed sequence and a terminator sequence, the terminator sequence including the sequence of nine connected nucleobases (A/T/G), (A/T/G), T, A, A, A, (A/T/G/C), (A/T/G/C), (A/G/C);

The annealed sequence in the reverse primer of (f) and the annealed sequence in the reverse primer of (c') may be identical enough that an amplified product can be obtained in the PCR reaction of step 2, but need not be completely identical sequences so as long as the sequences are partially identical. From a viewpoint of efficient performance of the PCR reaction, an example using identical annealed sequences can be given as a favorable example. In addition, the primers of (a), (c'), and (f) can be provided as a kit for producing a double-stranded linear DNA for RNA expression in mammalian cells and the like. Such a kit may also include, in addition to the aforementioned primers, a buffer, dNTPs, a template for a control, and the like.

Figure 3:
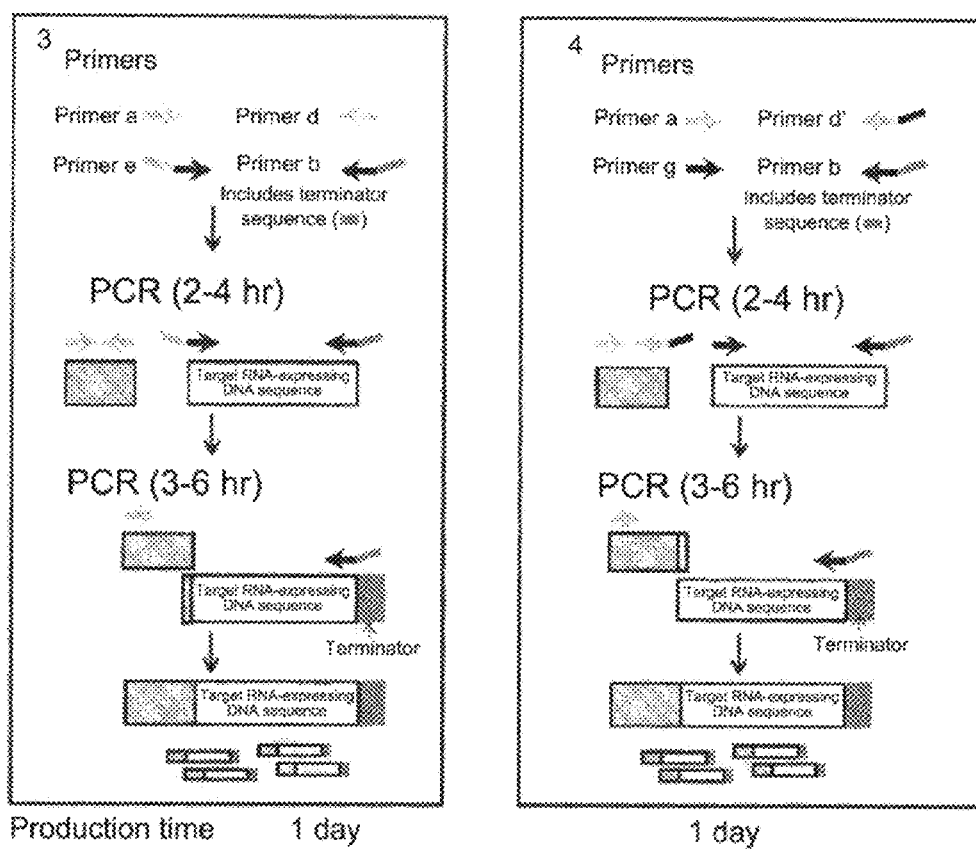
FIG. 3 shows overviews 3 and 4 of the method for producing linear DNA in the present invention.

3. Case-1 when a promoter sequence DNA and a target RNA-expressing DNA sequence are respectively used as a template and the terminator sequence is bound in one step (FIG. 3, left panel):

In a case where no construct is present having the target RNA-expressing DNA sequence connected downstream of the targeted promoter, the linear DNA according to the present invention can be produced using the PCR reaction according to steps 1 to 3 below.

<Step 1>

With the promoter sequence DNA as the template, primers according to (a) and (d) below are employed to produce, with the PCR method, DNA composed of the promoter sequence.

(a) Forward primer specific to promoter sequence;

(d) Reverse primer specific to promoter sequence (a reverse primer for amplification of a promoter sequence composed of a complementary sequence of a specific sequence in the promoter);

<Step 2>

With the target RNA-expressing DNA sequence as the template, primers according to (e) and (b) below are employed to produce, with the PCR method, DNA that includes, in order, a portion of a promoter sequence, a target RNA-expressing DNA sequence, and a terminator sequence.

(e) Forward primer composed of a DNA sequence that includes, in order, a region on a C-terminus side of the promoter sequence and a specific sequence of the target RNA-expressing DNA sequence to be amplified;

(b) Reverse primer composed of a complementary sequence of a DNA sequence that includes, in order, a specific sequence of the target RNA-expressing DNA sequence to be amplified and a terminator sequence, the terminator sequence being composed of between 30 and 200 nucleobases and including the sequence of nine connected nucleobases (A/T/G), (A/T/G), T, A, A, A, (A/T/G/C), (A/T/G/C), (A/G/C);

<Step 3>

With an amplified product obtained in steps 1 and 2 as the template, primers according to (a) and (b) below can be employed to amplify, with the PCR method, DNA that includes, in order, the promoter sequence, the target RNA-expressing DNA sequence, and the terminator sequence, and to produce the linear DNA according to the present invention.

(a) Forward primer specific to promoter sequence;

(b) Reverse primer composed of a complementary sequence of a DNA sequence that includes, in order, a specific sequence of a target RNA-expressing DNA sequence to be amplified and a terminator sequence, the terminator sequence being composed of between 30 and 200 nucleobases and including the sequence of nine connected nucleobases (A/T/G), (A/T/G), T, A, A, A, (A/T/G/C), (A/T/G/C), (A/G/C);

In addition, the primers of (a), (b), (d), and (e) can be provided as a kit for producing a double-stranded linear DNA for RNA expression in mammalian cells and the like. Such a kit may also include, in addition to the aforementioned primers, a buffer, dNTPs, a template for a control, and the like.

4. Case-2 when a promoter sequence DNA and target RNA-expressing DNA sequence DNA are respectively used as a template and the terminator sequence is bound in one step (FIG. 3, right panel):

In a case where no construct is present having the target RNA-expressing DNA sequence connected downstream of the targeted promoter, the linear DNA according to the present invention can be produced using the PCR reaction according to steps 1 to 3 below.

<Step 1>

With the promoter sequence DNA as the template, primers according to (a) and (d') below are employed to produce, with the PCR method, DNA composed of a sequence that includes, in order, the promoter sequence and a portion of the target RNA-expressing DNA sequence to be amplified.

(a) Forward primer specific to promoter sequence;

(d') Reverse primer composed of a complementary sequence of a DNA sequence that includes, in order, a promoter-specific sequence and a region on an N-terminus side of the target RNA-expressing DNA sequence to be amplified;

<Step 2>

With the target RNA-expressing DNA sequence as the template, primers according to (g) and (b) below are employed to produce, with the PCR method, DNA composed of a sequence that includes, in order, a target RNA-expressing DNA sequence and a terminator sequence.

(g) Forward primer composed of a specific sequence of the target RNA-expressing DNA sequence to be amplified;

(b) Reverse primer composed of a complementary sequence of a DNA sequence that includes, in order, a specific sequence of a target RNA-expressing DNA sequence to be amplified and a terminator sequence, the terminator sequence being composed of between 30 and 200 nucleobases and including the sequence of nine connected nucleobases (A/T/G), (A/T/G), T, A, A, A, (A/T/G/C), (A/T/G/C), (A/G/C);

<Step 3>

With an amplified product obtained in steps 1 and 2 as the template, primers according (a) and (b) below can be employed to amplify, with the PCR method, DNA that includes, in order, the promoter sequence, the target RNA-expressing DNA sequence, and the terminator sequence, and to produce the linear DNA according to the present invention.

(a) Forward primer specific to promoter sequence;

(b) Reverse primer composed of a complementary sequence of a DNA sequence that includes, in order, a specific sequence of a target RNA-expressing DNA sequence to be amplified and a terminator sequence, the terminator sequence being composed of between 30 and 300 nucleobases and including the sequence of nine connected nucleobases (A/T/G), (A/T/G), T, A, A, A, (A/T/G/C), (A/T/G/C), (A/G/C);

In addition, the primers of (a), (b), (d'), and (g) can be provided as a kit for producing a double-stranded linear DNA for RNA expression in mammalian cells and the like. Such a kit may also include, in addition to the aforementioned primers, a buffer, dNTPs, a template for a control, and the like.

Figure 4:
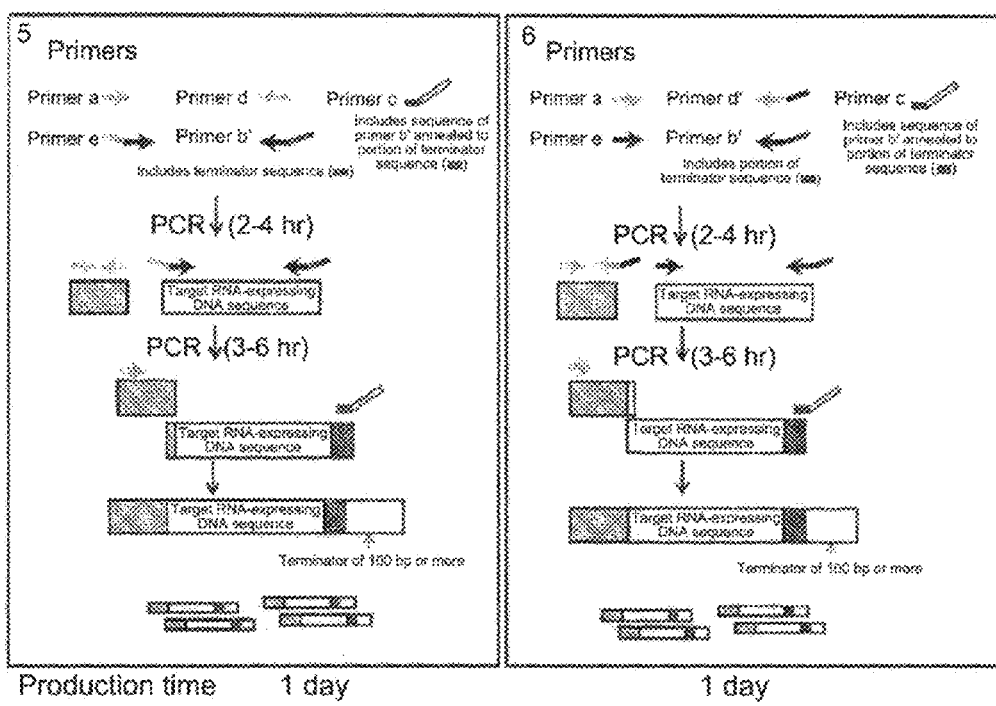
FIG. 4 shows overviews 5 and 6 of the method for producing linear DNA in the present invention.

5. Case-1 when a promoter sequence DNA and a target RNA-expressing DNA sequence are respectively used as a template and the terminator sequence is bound in two steps (FIG. 4, left panel):

In a case where no construct is present having the target RNA-expressing DNA sequence connected downstream of the targeted promoter, the linear DNA according to the present invention can be produced using the PCR reaction according to steps 1 to 3 below.

<Step 1>

With the promoter sequence DNA as the template, primers according to (a) and (d) below are employed to produce, with the PCR method, DNA composed of the promoter sequence.

(a) Forward primer specific to promoter sequence;

(d) Reverse primer specific to promoter sequence;

<Step 2>

With a target RNA-expressing DNA sequence as the template, primers according to (e) and (b') below are employed to produce, with the PCR method, DNA composed of a sequence that includes, in order, a portion of a promoter sequence, a target RNA-expressing DNA sequence, and a terminator sequence.

(e) Forward primer composed of a DNA sequence that includes, in order, a region on a C-terminus side of a promoter sequence and a specific sequence of the target RNA-expressing DNA sequence to be amplified;

(b') Reverse primer composed of a complementary sequence of a DNA sequence that includes, in order, the specific sequence of the target RNA-expressing DNA sequence to be amplified and the terminator sequence;

<Step 3>

With an amplified product obtained in steps 1 and 2 as the template, primers according to (a) and (c) below can be employed to amplify, with the PCR method, DNA that includes, in order, the promoter sequence, the target RNA-expressing DNA sequence, and the terminator sequence, and to produce the linear DNA according to the present invention.

(a) Forward primer specific to promoter sequence;

(c) Reverse primer composed of complementary sequence of terminator sequence;

The reverse primer of (b') need not include the sequence of nine connected nucleobases (A/T/G), (A/T/G), T, A, A, A, (A/T/G/C), (A/T/G/C), (A/G/C) in the terminator sequence. Instead, it is sufficient for the terminator sequence to include the sequence of nine connected nucleobases (A/T/G), (A/T/G), T, A, A, A, (A/T/G/C), (A/T/G/C), (A/G/C) in the linear of the present invention, which includes, in order, the promoter sequence, the target RNA-expressing DNA sequence, and the terminator sequence, the linear being amplified by the PCR reaction of step 3. An example can be given in which the linear of the present invention is, for example, produced not by including the nine connected nucleobases (A/T/G), (A/T/G), T, A, A, A, (A/T/G/C), (A/T/G/C), (A/G/C) in the reverse primer of (b'), but is instead produced by the reverse primer of (c) including the sequence of nine connected nucleobases. In addition, the primers of (a), (b'), (c), (d), and (e) can be provided as a kit for producing a double-stranded linear DNA for RNA expression in mammalian cells and the like. Such a kit may also include, in addition to the aforementioned primers, a buffer, dNTPs, a template for a control, and the like.

As a different mode, the linear DNA of the present invention can be produced by the PCR reaction according to steps 1 to 3, below, using an annealed sequence.

<Step 1>

With the promoter sequence DNA as the template, primers according to (a) and (d) below are employed to produce, with the PCR method, DNA composed of the promoter sequence.

(a) Forward primer specific to promoter sequence;
(d) Reverse primer specific to promoter sequence;

<Step 2>

With a target RNA-expressing DNA sequence as the template, primers according to (e) and (f) below are employed to produce, with the PCR method, DNA composed of a sequence that includes, in order, a portion of a promoter sequence, a target RNA-expressing DNA sequence, and an annealed sequence.

(e) Forward primer composed of a DNA sequence that includes, in order, a region on a C-terminus side of the promoter sequence and a specific sequence of the target RNA-expressing DNA sequence to be amplified;

(f) Reverse primer composed of a complementary sequence of a DNA sequence that includes, in order, the specific sequence of the target RNA-expressing DNA sequence to be amplified and the annealed sequence;

<Step 3>

With an amplified product obtained in steps 1 and 2 as the template, primers according (a) and (c') below can be employed to amplify, with the PCR method, DNA composed of a sequence that includes, in order, the promoter sequence, the target RNA-expressing DNA sequence, the annealed sequence, and the terminator sequence, and to produce the linear DNA according to the present invention.

(a) Forward primer specific to promoter sequence;
(c') Reverse primer composed of a complementary sequence of a DNA sequence that includes, in order, an annealed sequence and a terminator sequence, the terminator sequence including the sequence of nine connected nucleobases (A/T/G), (A/T/G), T, A, A, A, (A/T/G/C), (A/T/G/C), (A/G/C);

The annealed sequence in the reverse primer of (f) and the annealed sequence in the reverse primer of (c') may be identical enough that an amplified product can be obtained in the PCR reaction of step 3, but need not be completely identical sequences so as long as the sequences are partially identical. From a viewpoint of efficient performance of the PCR reaction, an example using identical annealed sequences can be given as a favorable example. In addition, the primers of (a), (c'), (d), (e), and (f) can be provided as a kit for producing a double-stranded linear DNA for RNA expression in mammalian cells and the like. Such a kit may also include, in addition to the aforementioned primers, a buffer, dNTPs, a template for a control, and the like.

6. Case-2 when a promoter sequence DNA and a target RNA-expressing DNA sequence are respectively used as a template and the terminator sequence is bound in two steps (FIG. 4, right panel):

In a case where no construct is present having the target RNA-expressing DNA sequence connected downstream of the targeted promoter, the linear DNA according to the present invention can be produced using the PCR reaction according to steps 1 to 3 below.

<Step 1>

With the promoter sequence DNA as the template, primers according to (a) and (d') below are employed to produce, with the PCR method, DNA composed of a sequence that includes, in order, the promoter sequence and a portion of the target RNA-expressing DNA sequence to be amplified.

(a) Forward primer specific to promoter sequence;

(d') Reverse primer composed of a complementary sequence of a DNA sequence that includes, in order, a specific sequence of the promoter and a region on an N-terminus side of the target RNA-expressing DNA sequence to be amplified;

<Step 2>

With a target RNA-expressing DNA sequence as the template, primers according to (g) and (b') below are employed to amplify, with the PCR method, DNA that includes, in order, a target RNA-expressing DNA sequence and a terminator sequence.

(g) Forward primer composed of a specific sequence of the target RNA-expressing DNA sequence to be amplified;

(b') Reverse primer composed of a complementary sequence of a DNA sequence that includes, in order, the specific sequence of the target RNA-expressing DNA sequence to be amplified and the terminator sequence;

<Step 3>

With an amplified product obtained in steps 1 and 2 as the template, primers according to (a) and (c) below can be employed to amplify, with the PCR method, DNA composed of a sequence that includes, in order, the promoter sequence, the target RNA-expressing DNA sequence, and the terminator sequence, and to produce the linear DNA according to the present invention.

(a) Forward primer specific to promoter sequence;
(c) Reverse primer composed of complementary sequence of terminator sequence;

The reverse primer of (b') need not include the sequence of nine connected nucleobases (A/T/G), (A/T/G), T, A, A, A, (A/T/G/C), (A/T/G/C), (A/G/C) in the terminator sequence. Instead, it is sufficient for the terminator sequence to include the sequence of nine connected nucleobases (A/T/G), (A/T/G), T, A, A, A, (A/T/G/C), (A/T/G/C), (A/G/C) in the linear of the present invention, which includes, in order, the promoter sequence, the target RNA-expressing DNA sequence, and the terminator sequence, the linear being amplified by the PCR reaction of step 3. An example can be given in which the linear of the present invention is produced, for example, not by including the nine connected nucleobases (A/T/G), (A/T/G), T, A, A, A, (A/T/G/C), (A/T/G/C), (A/G/C) in the reverse primer of (b'), but is instead produced by the reverse primer of (c) including the sequence of nine connected nucleobases. In addition, the primers of (a), (b'), (c), (d'), and (g) can be provided as a kit for producing a double-stranded linear DNA for RNA expression in mammalian cells and the like. Such a kit may also include, in addition to the aforementioned primers, a buffer, dNTPs, a template for a control, and the like.

As a different mode, the linear DNA of the present invention can be produced by the PCR reaction according to steps 1 to 3, below, using an annealed sequence.

<Step 1>

With the promoter sequence DNA as the template, primers according to (a) and (d') below are employed to produce, with the PCR method, DNA composed of a sequence that includes, in order, the promoter sequence and a portion of the target RNA-expressing DNA sequence to be amplified.

(a) Forward primer specific to promoter sequence;

(d') Reverse primer composed of a complementary sequence of a DNA sequence that includes, in order, a specific sequence of the promoter and a region on an N-terminus side of the target RNA-expressing DNA sequence to be amplified;

<Step 2>

With a target RNA-expressing DNA sequence as a template, primers according to (g) and (f) below are employed to produce, with the PCR method, DNA composed of a sequence that includes, in order, a target RNA-expressing DNA sequence and an annealed sequence.

(g) Forward primer composed of a specific sequence of the target RNA-expressing DNA sequence to be amplified;

(f) Reverse primer composed of a complementary sequence of a DNA sequence that includes, in order, the specific sequence of the target RNA-expressing DNA sequence to be amplified and the annealed sequence;

<Step 3>

With an amplified product obtained in steps 1 and 2 as the template, primers according to (a) and (c') below can be employed to amplify, with the PCR method, DNA that includes, in order, the promoter sequence, the target RNA-expressing DNA sequence, the annealed sequence, and the terminator sequence, and to produce the linear DNA according to the present invention.

(a) Forward primer specific to promoter sequence;

(c') Reverse primer composed of a complementary sequence of a DNA sequence that includes, in order, an annealed sequence and a terminator sequence, the terminator sequence including the sequence of nine connected nucleobases (A/T/G), (A/T/G), T, A, A, A, (A/T/G/C), (A/T/G/C), (A/G/C);

The annealed sequence in the reverse primer of (f) and the annealed sequence in the reverse primer of (c') may be identical enough that an amplified product can be obtained in the PCR reaction of step 3, but need not be completely identical sequences so as long as the sequences are partially identical. From a viewpoint of efficient performance of the PCR reaction, an example using identical annealed sequences can be given as a favorable example. In addition, the primers of (a), (c'), (d'), (f), and (g) can be provided as a kit for producing a double-stranded linear DNA for RNA expression in mammalian cells and the like. Such a kit may also include, in addition to the aforementioned primers, a buffer, dNTPs, a template for a control, and the like.

As noted above, when using an annealed sequence, a terminator sequence can be connected to a target RNA-expressing DNA sequence via the annealed sequence. Therefore, a linear DNA for RNA expression having various terminator sequences bound to a certain target RNA-expressing DNA sequence can be readily produced. Similarly, DNA having a target RNA-expressing DNA sequence connected to a promoter sequence via an annealed sequence can also be produced. Hereafter, an illustration is given of a method for amplifying, using a PCR reaction, a linear DNA that includes, in order, a promoter sequence, an annealed sequence 1, a target RNA-expressing DNA sequence, an annealed sequence 2, and a terminator sequence.

<Step 1>

With a promoter sequence DNA as the template, primers according to (a) and (h) below are employed to produce, with the PCR method, DNA composed of a sequence that includes, in order, the promoter sequence and the annealed sequence 1.

(a) Forward primer specific to promoter sequence;

(h) Reverse primer composed of a complementary sequence of a DNA sequence that includes, in order, the promoter sequence and the annealed sequence 1;

<Step 2>

With a target RNA-expressing DNA sequence as the template, primers according to (i) and (f) below are employed to amplify, using the PCR method, an amplified product composed of a sequence that includes, in order, the annealed sequence 1, the target RNA-expressing DNA sequence, and the annealed sequence 2.

(i) Forward primer composed of the annealed sequence 1 and a specific sequence of the target RNA-expressing DNA sequence to be amplified;

(f) Reverse primer composed of a complementary sequence of a DNA sequence that includes, in order, the specific sequence of the target RNA-expressing DNA sequence to be amplified and the annealed sequence 2;

<Step 3>

With an amplified product obtained in steps 1 and 2 as the template, primers according to (a) and (c') below can be employed to amplify, using the PCR method, DNA that includes, in order, the promoter sequence, the annealed sequence 1, the target RNA-expressing DNA sequence, the annealed sequence 2, and the terminator sequence, and to produce the linear DNA according to the present invention.

(a) Forward primer specific to promoter sequence;

(c') Reverse primer composed of a complementary sequence of a DNA sequence that includes, in order, the annealed sequence 2 and the terminator sequence, the terminator sequence including the sequence of nine connected nucleobases (A/T/G), (A/T/G), T, A, A, A, (A/T/G/C), (A/T/G/C), (A/G/C);

The annealed sequence 1 in the reverse primer of (h) and the annealed sequence 1 in the forward primer of (i) may be identical enough that an amplified product can be obtained in the PCR reaction of step 3, but need not be completely identical sequences so as long as the sequences are partially identical. From a viewpoint of efficient performance of the PCR reaction, an example using identical annealed sequences can be given as a favorable example. The annealed sequence 2 in the reverse primer of (f) and the annealed sequence 2 in the reverse primer of (c') may be identical enough that an amplified product can be obtained in the PCR reaction of step 3, but need not be completely identical sequences so as long as the sequences are partially identical. From a viewpoint of efficient performance of the PCR reaction, an example using identical annealed sequences can be given as a favorable example.

As long as sequences of the annealed sequence 1 and the annealed sequence 2 can obtain the PCR amplified product in steps 2 or 3, they may be identical sequences. However, in order to efficiently perform the PCR reaction and to obtain DNA that is the target amplified product and that includes, in order, the promoter sequence, the annealed sequence 1, the target RNA-expressing DNA sequence, the annealed sequence 2, and the terminator sequence, the sequences of the annealed sequence 1 and the annealed sequence 2 are preferably different DNA sequences. Using the annealed sequence 1, which includes a start codon ATG, the ATG and a translation frame can be matched up to connect the DNA sequence causing expression and thus produce the linear DNA of the present invention. This is useful in a case using a protein-coding DNA sequence that does not contain the start codon. Moreover, a Kozak sequence can be included in the annealed sequence 1 and, by including the Kozak sequence and a start codon located such that the Kozak sequence functions, protein expression can be enhanced. The annealed sequence 2 can also be used, the annealed sequence 2 being located such that one or more stop codons TAA, TAG, or TGA function in a specific translation frame or in all three translation frames. In addition, the primers of (a), (c'), (i), (f), and (h) can be provided as a kit for producing a double-stranded linear DNA for RNA expression in mammalian cells and the like. Such a kit may also include, in addition to the aforementioned primers, a buffer, dNTPs, a template for a control, and the like.

Figure 5:
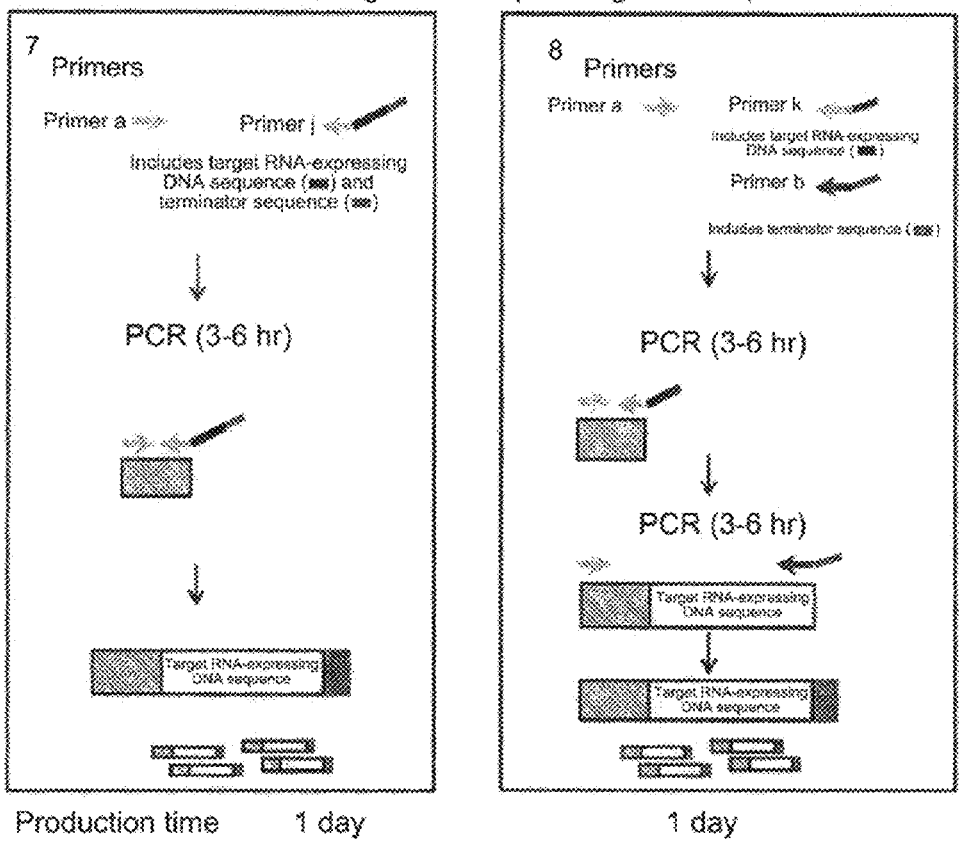
FIG. 5 shows overviews 7 and 8 of the method for producing linear DNA in the present invention.

7. Case-1 when a promoter sequence DNA is used as a template and a target RNA-expressing DNA sequence and a terminator sequence are bound in one step by defining a complementary sequence of the target RNA-expressing DNA sequence on a reverse primer, without employing a template of the target RNA-expressing DNA sequence (FIG. 5, left panel):

In a case where no construct is present having the target RNA-expressing DNA sequence connected downstream of the targeted promoter, the linear DNA according to the present invention can be produced using the PCR reaction according to step 1 below.

<Step 1>

With a promoter sequence DNA as the template, primers according (a) and (j) below can be employed to amplify, using the PCR method, DNA that includes, in order, the promoter sequence, the target RNA-expressing DNA sequence, and the terminator sequence, and to produce the linear DNA according to the present invention.

(a) Forward primer specific to promoter sequence;

(j) Reverse primer composed of a complementary sequence of a DNA sequence that includes, in order, a region on the C-terminus side of a promoter sequence, a specific sequence of a target RNA-expressing DNA sequence to be amplified, and a terminator sequence, the terminator sequence being composed of between 30 and 200 nucleobases and including the sequence of nine connected nucleobases (A/T/G), (A/T/G), T, A, A, A, (A/T/G/C), (A/T/G/C), (A/G/C);

In addition, the primers of (a) and (j) can be provided as a kit for producing a double-stranded linear DNA for RNA expression in cells. Such a kit may also include, in addition to the aforementioned primers, a buffer, dNTPs, a template for a control, and the like.

8. Case-2 when a promoter sequence DNA is used as a template and a target RNA-expressing DNA sequence and a terminator sequence are bound in one step by defining a complementary sequence of the target RNA-expressing DNA sequence on a reverse primer, without employing a template of the target RNA-expressing DNA sequence (FIG. 5, panel right):

In a case where no construct is present having the target RNA-expressing DNA sequence connected downstream of the targeted promoter, the linear DNA according to the present invention can be produced using the PCR reaction according to steps 1 and 2 below.

<Step 1>

With a promoter sequence DNA as the template, primers according to (a) and (k) below are employed to produce, with the PCR method, DNA composed of a sequence that includes, in order, the promoter sequence and an entire length of the target RNA-expressing DNA sequence to be amplified.

(a) Forward primer specific to promoter sequence;

(k) Reverse primer composed of a complementary sequence of a DNA sequence that includes, in order, a region on a C-terminus side of the promoter sequence and a specific sequence of the entire length of the target RNA-expressing DNA sequence to be amplified;

<Step 2>

With an amplified product obtained in step 1 as the template, primers according to (a) and (b) below can be employed to amplify, with the PCR method, DNA that includes, in order, the promoter sequence, the target RNA-expressing DNA sequence, and the terminator sequence, and to produce the linear DNA according to the present invention.

(a) Forward primer specific to promoter sequence;

(b) Reverse primer composed of a complementary sequence of a DNA sequence that includes, in order, a specific sequence of a target RNA-expressing DNA sequence to be amplified (produced in step 1) and a terminator sequence, the terminator sequence being composed of between 30 and 300 nucleobases and including the sequence of nine connected nucleobases (A/T/G), (A/T/G), T, A, A, A, (A/T/G/C), (A/T/G/C), (A/G/C);

In addition, the primers of (a), (b), and (k) can be provided as a kit for producing a double-stranded linear DNA for RNA expression in cells. Such a kit may also include, in addition to the aforementioned primers, a buffer, dNTPs, a template for a control, and the like.

As a different mode, the linear DNA of the present invention can be produced by the PCR reaction according to steps 1 and 2, below, using an annealed sequence.

<Step 1>

With a promoter sequence DNA as the template, primers according to (a) and (l) below are employed to produce, with the PCR method, DNA composed of a sequence that includes, in order, the promoter sequence and an entire length of the target RNA-expressing DNA sequence to be amplified.

(a) Forward primer specific promoter sequence;

(l) Reverse primer composed of a complementary sequence of a DNA sequence that includes, in order, a region on a C-terminus side of the promoter sequence, the entire length of the target RNA-expressing DNA sequence to be amplified, and a specific sequence of the annealed sequence;

<Step 2>

With an amplified product obtained in step 1 as the template, primers according to (a) and (c') below can be employed to amplify, with the PCR method, DNA composed of a sequence that includes, in order, the promoter sequence, the target RNA-expressing DNA sequence, the annealed sequence, and the terminator sequence, and to produce the linear DNA according to the present invention.

(a) Forward primer specific to promoter sequence;

(c') Reverse primer composed of a complementary sequence of a DNA sequence that includes, in order, the annealed sequence and the terminator sequence, the terminator sequence including the sequence of nine connected nucleobases (A/T/G), (A/T/G), T, A, A, A, (A/T/G/C), (A/T/G/C), (A/G/C);

The annealed sequence in the reverse primer of (l) and the annealed sequence in the reverse primer of (c') may be identical enough that an amplified product can be obtained in the PCR reaction of step 2, but need not be completely identical sequences so as long as the sequences are partially identical. From a viewpoint of efficient performance of the PCR reaction, an example using identical annealed sequences can be given as a favorable example. In addition, the primers of (a), (c'), and (l) can be provided as a kit for producing a double-stranded linear DNA for RNA expression in mammalian cells and the like. Such a kit may also include, in addition to the aforementioned primers, a buffer, dNTPs, a template for a control, and the like.

Figure 6:
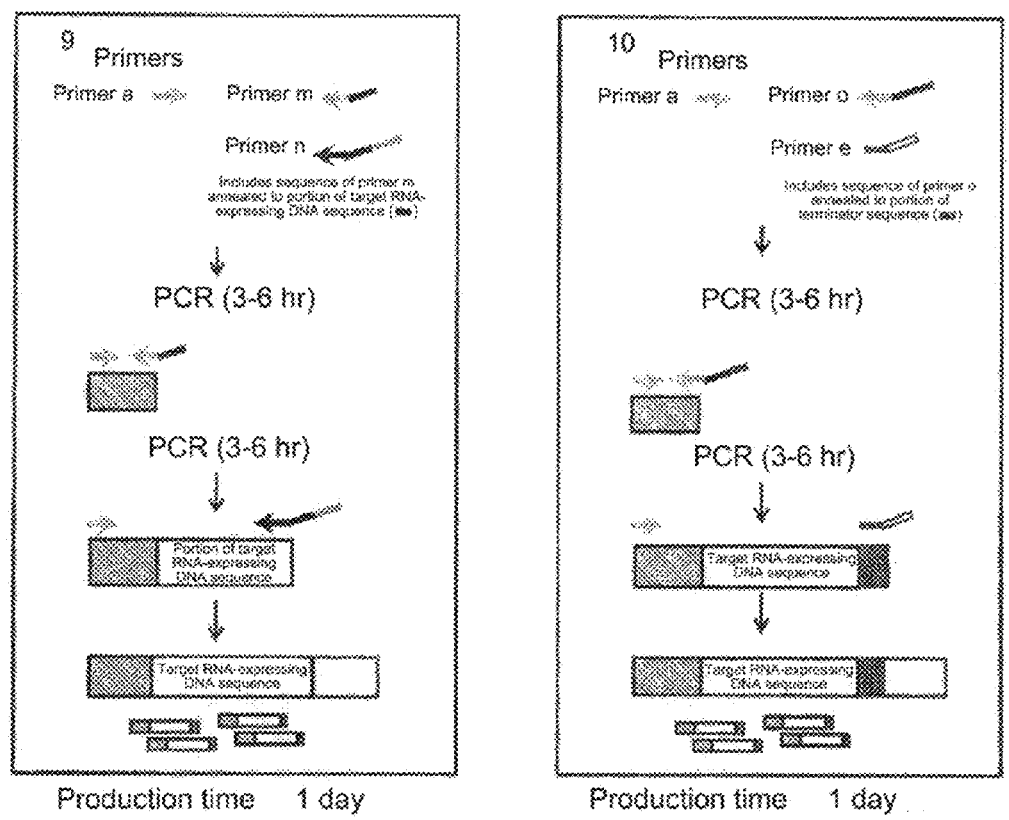
FIG. 6 shows overviews 9 and 10 of the method for producing linear DNA in the present invention.

9. Case-3 when a promoter sequence DNA is used as a template and a target RNA-expressing DNA sequence and a terminator sequence are bound in one step by defining a complementary sequence of the target RNA-expressing DNA sequence on a reverse primer, without employing a template of the target RNA-expressing DNA sequence (FIG. 6, panel left):

In a case where no construct is present having the target RNA-expressing DNA sequence connected downstream of the targeted promoter, the linear DNA according to the present invention can be produced using the PCR reaction according to steps 1 and 2 below.

<Step 1>

With a promoter sequence DNA as the template, primers according to (a) and (m) below are employed to produce, with the PCR method, a DNA composed of a sequence that includes, in order, the promoter sequence and a region on an N-terminus side of the target RNA-expressing DNA sequence to be amplified.

(a) Forward primer specific to promoter sequence;

(m) Reverse primer composed of a complementary sequence of a DNA sequence that includes, in order, a region on a C-terminus side of the promoter sequence and a specific sequence on a portion including a region on an N-terminus side of the target RNA-expressing DNA sequence to be amplified;

<Step 2>

With an amplified product obtained in step 1 as the template, primers according to (a) and (n) below can be employed to amplify, with the PCR method, DNA that includes, in order, the promoter sequence, the target RNA-expressing DNA sequence, and the terminator sequence, and to produce the linear DNA according to the present invention.

(a) Forward primer specific to promoter sequence;

(n) Reverse primer composed of a complementary sequence of a DNA sequence that includes, in order, a specific sequence on a portion of the region on the C-terminus side of the target RNA-expressing DNA sequence to be amplified (produced in step 1) and a terminator sequence, the terminator sequence being composed of between 30 and 300 nucleobases and including the sequence of nine connected nucleobases (A/T/G), (A/T/G), T, A, A, A, (A/T/G/C), (A/T/G/C), (A/G/C);

In addition, the primers of (a), (m), and (n) can be provided as a kit for producing a double-stranded linear DNA for RNA expression in cells. Such a kit may also include, in addition to the aforementioned primers, a buffer, dNTPs, a template for a control, and the like.

10. Case-4 when a promoter sequence DNA is used as a template and a target RNA-expressing DNA sequence and a terminator sequence are bound in two steps by defining a complementary sequence of the target RNA-expressing DNA sequence on a reverse primer, without employing a template of the target RNA-expressing DNA sequence (FIG. 6, right panel):

In a case where no construct is present having the target RNA-expressing DNA sequence connected downstream of the targeted promoter, the linear DNA according to the present invention can be produced using the PCR reaction according to steps 1 and 2 below.

<Step 1>

With a promoter sequence DNA as the template, primers according to (a) and (o) below are employed to produce, with the PCR method, DNA composed of a sequence that includes, in order, the promoter sequence and an entire length of the target RNA-expressing DNA sequence to be amplified.

(a) Forward primer specific to promoter sequence;

(o) Reverse primer composed of a complementary sequence of a DNA sequence that includes, in order, a specific sequence of the promoter, the entire length of the target RNA-expressing DNA sequence to be amplified, and the terminator sequence;

<Step 2>

With an amplified product obtained in step 1 as the template, primers according to (a) and (c) below can be employed to amplify, with the PCR method, DNA that includes, in order, the promoter sequence, the target RNA-expressing DNA sequence, and the terminator sequence, and to produce the linear DNA according to the present invention.

(a) Forward primer specific to promoter sequence;

(c) Reverse primer composed of a complementary sequence of a terminator sequence;

The reverse primer of (o) need not include the sequence of nine connected nucleobases (A/T/G), (A/T/G), T, A, A, A, (A/T/G/C), (A/T/G/C), (A/G/C) in the terminator sequence. Instead, it is sufficient for the terminator sequence to include the sequence of nine connected nucleobases (A/T/G), (A/T/G), T, A, A, A, (A/T/G/C), (A/T/G/C), (A/G/C) in the linear DNA of the present invention, which includes, in order, the promoter sequence, the target RNA-expressing DNA sequence, and the terminator sequence, the linear DNA being amplified by the PCR reaction of step 2. An example can be given in which the linear DNA of the present invention is produced, for example, not by including the nine connected nucleobases (A/T/G), (A/T/G), T, A, A, A, (A/T/G/C), (A/T/G/C), (A/G/C) in the reverse primer of (o), but is instead produced by the reverse primer of (c) including the sequence of nine connected nucleobases. In addition, the primers of (a), (c), and (o) can be provided as a kit for producing a double-stranded linear DNA for RNA expression in cells. Such a kit may also include, in addition to the aforementioned primers, a buffer, dNTPs, a template for a control, and the like.

As a different mode, the linear DNA of the present invention can be produced by the PCR reaction according to steps 1 to 3, below, using an annealed sequence.

<Step 1>

With a promoter sequence DNA as the template, primers according to (a) and (p) below are employed to produce, with the PCR method, DNA composed of a sequence that includes, in order, the promoter sequence, an entire length of the target RNA-expressing DNA sequence to be amplified, and the annealed sequence.

(a) Forward primer specific to promoter sequence;

(p) Reverse primer composed of a complementary sequence of a DNA sequence that includes, in order, a specific sequence of the promoter, the entire length of the target RNA-expressing DNA sequence to be amplified, and the annealed sequence;

<Step 2>

With an amplified product obtained in step 1 as the template, primers according to (a) and (c') below can be employed to amplify, with the PCR method, DNA that includes, in order, the promoter sequence, the target RNA-expressing DNA sequence, the annealed sequence, and the terminator sequence, and to produce the linear DNA according to the present invention.

(a) Forward primer specific to promoter sequence;

(c') Reverse primer composed of a complementary sequence of a DNA sequence that includes, in order, the annealed sequence and the terminator sequence, the terminator sequence including the sequence of nine connected nucleobases (A/T/G), (A/T/G), T, A, A, A, (A/T/G/C), (A/T/G/C), (A/G/C);

The annealed sequence in the reverse primer of (p) and the annealed sequence in the reverse primer of (c') may be identical enough that an amplified product can be obtained in the PCR reaction of step 2, but need not be completely identical sequences so as long as the sequences are partially identical. From a viewpoint of efficient performance of the PCR reaction, an example using identical annealed sequences can be given as a favorable example. In addition, the primers of (a), (c'), and (p) can be provided as a kit for producing a double-stranded linear DNA for RNA expression in mammalian cells and the like. Such a kit may also include, in addition to the aforementioned primers, a buffer, dNTPs, a template for a control, and the like.

A method of RNA expression using the linear DNA of the present invention may be a method using transfection of the double-stranded linear DNA for RNA expression according to the present invention into mammalian cells and the like. Examples of a method transfecting the linear DNA of the present invention into cells can include a liposome method as a method of gene transfer, a lipofection method, a microinjection method, a DEAE dextran method, a calcium phosphate method, an electroporation method, and the like. The method transfecting the linear DNA of the present invention into cells can be performed with commercially available transfection reagents such as Lipofectin® Reagent, Lipofectamine®, Lipofectamine® 2000 Reagent (made by Invitrogen Corporation), SuperFect® Transfection Reagent (made by Qiagen), FuGENE® HD Transfection Reagent and FuGENE® 6 Transfection Reagent (made by Roche), and the like, as well as by manual methods in wide use in the art. A method of confirming RNA expression in the cells using the linear DNA of the present invention is not particularly limited. A quantity can be determined by performing a luciferase assay using a luciferase gene in the target RNA-expressing DNA sequence, and detection can be performed with a routine method such as Western blotting, an ELISA method, and the like using an antibody.

The method of RNA expression using the linear DNA of the present invention enables quick and easy work performance. Therefore, development of a high level of throughput and automation by machines is possible, in which a large amount of samples are handled in parallel. Therefore, the method can be preferably applied to screening. For example, screening using mammalian cell expression linear DNA and the like can be performed that includes the steps (a) to (c), wherein: (a) the linear DNA of the present invention is produced for various genes; (b) the linear DNA is transfected to a cell culture; (c) a gene is selected in which an indicator is modified, as compared to control cells, by transfection of the linear DNA. In step (b), it is possible to use cells in which RNA expression caused by a plasmid has already occurred; to use cells stimulated by cytokine, a chemical substance, and the like; or to transfect a plurality of kinds of linear DNA. In step (c), it is possible to define the indicator with a method corresponding to an objective.

For example, in a case where a gene inhibiting cell division is screened, it is possible to select in step (c) a sample for which cell division is suppressed, the sample having few cells as compared to a control. Further, in a case where genes related to transmission of a certain signal are screened, in step (b) cells transfected with the linear DNA and a signal transmission luciferase reporter DNA can be stimulated with cytokine, and in step (c) a sample can be selected using expression of the luciferase reporter as an indicator, the sample having signal transmission enhanced or suppressed in a stimulus-dependent or stimulus-independent manner.

The present invention is described in further detail below with reference to embodiments. The technical scope of the present invention, however, is not limited to the embodiments.

Embodiment 1

(Comparison of Gene Expression Using a Plasmid and Gene Expression Using Linear DNA)

Figure 7:
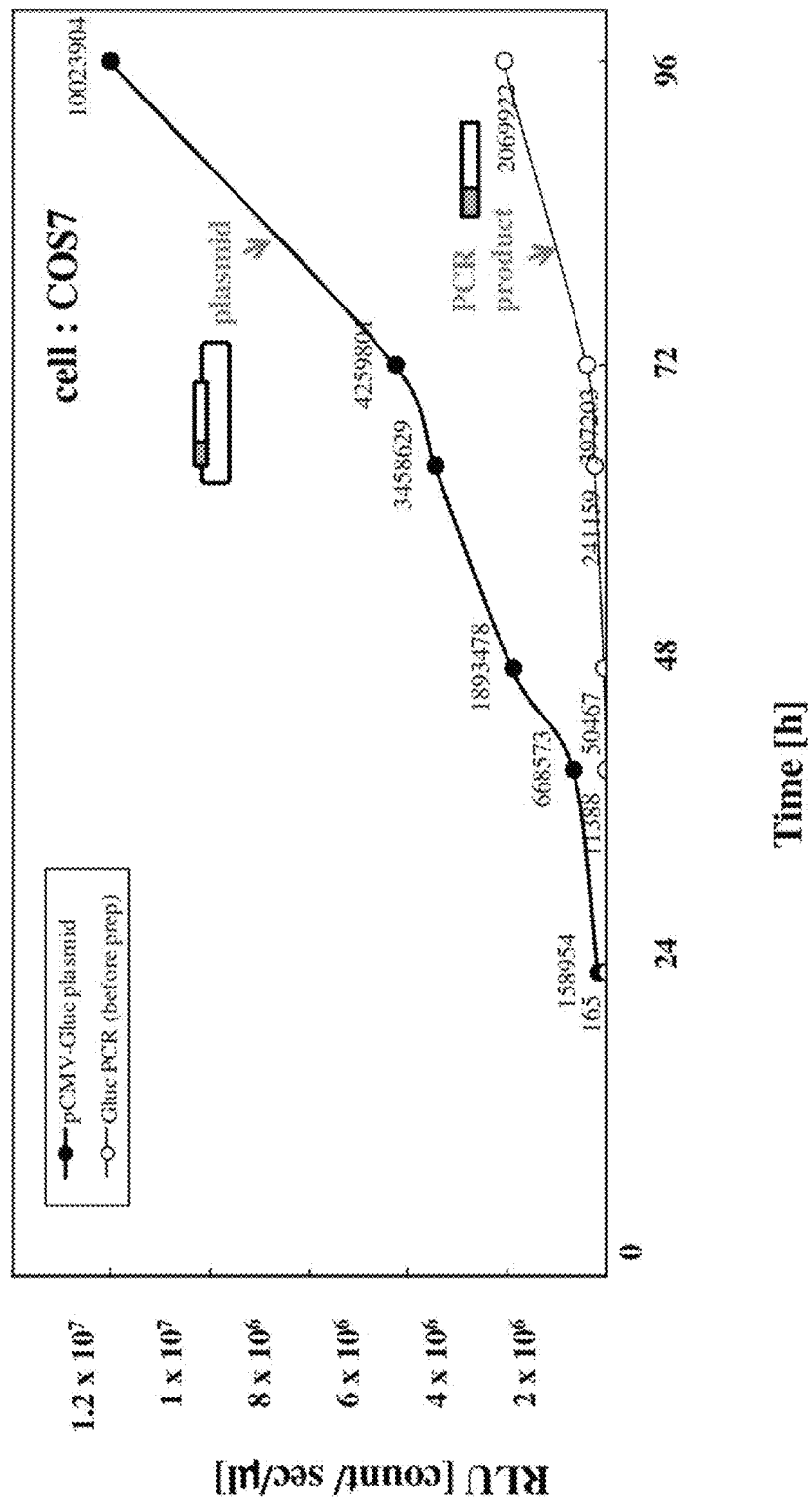
FIG. 7 illustrates that gene expression is markedly lower when using linear DNA in which plasmid vectors have been rendered into a linear form, as compared to a case using plasmid vectors.

Using a secreted luciferase-expressing plasmid vector pCMV-Gluc (made by New England Biolabs) as the template, a luciferase-expressing linear DNA was produced using the PCR method by employing primers of SEQ ID NOS: 4 and 12, the luciferase-expressing linear DNA being composed of a promoter, a secreted luciferase gene, and a plasmid-derived terminator sequence. The PCR was performed using KOD plus polymerase (made by Toyobo Co., Ltd.) in adherence to the recommended protocol therefor. Detailed conditions are noted below. Final concentrations were adjusted to be, respectively, template: 50 pg/µL, forward primer: 0.3 µM, reverse primer: 0.3 µM, then cycles at 94° C. for 20 seconds, 55° C. for 30 seconds, and 68° C. for 2 minutes were carried out thirty times using an icycler thermal cycler (made by Bio-Rad). One hundred ng of the luciferase-expressing plasmid vector pCMV-Gluc or 100 ng of the luciferase-expressing linear DNA was dispensed using a FuGENE® HD Transfection Reagent kit (made by Roche) into 96 well plates such that there were 2000 cells per well, then was transfected to COST cells derived from twenty-hour-old African green monkey kidney. During a period of 24 to 96 hours thereafter, culture supernatant was collected six times, then an amount of secreted luciferase contained in each of the culture supernatants was measured with a GLOMAX 20/20 Luminometer (made by Promega) using a BioLux Gaussia Luciferase assay kit (made by New England Biolabs). Results are shown in FIG. 7. Gene expression was confirmed to be markedly lower when linear DNA was used, in comparison to using the plasmid vector, as was known up to this point.

Figure 8:
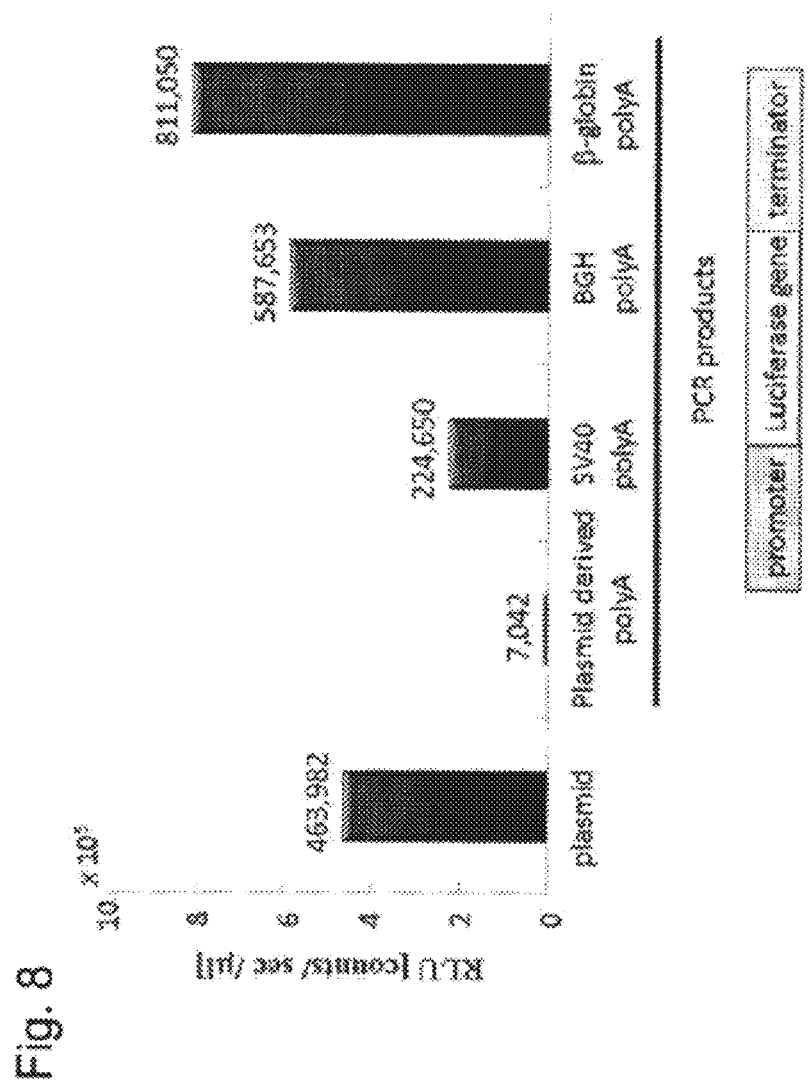
FIG. 8 illustrates that linear DNA (PCR amplified product) using an SV40 terminator sequence (SV40 poly(A)), BGH terminator sequence (BGH poly(A)), or β-globin terminator sequence (β-globin poly(A)) has an amount of luciferase (RLU) gene expression that is high in comparison to a case where a plasmid-derived terminator sequence (poly(A)) is used.

Under these circumstances, in order to investigate an effect of the terminator sequence in gene expression using linear DNA, a secreted luciferase gene was provided downstream of the CMV promoter to produce a luciferase-expressing linear DNA with the PCR method, the luciferase-expressing linear DNA having, downstream of the secreted luciferase gene, a plasmid poly(A), an SV40 terminator sequence (SEQ ID NO: 8), a BGH (bovine growth hormone) terminator sequence (SEQ ID NO: 9), or a β-globin terminator sequence (SEQ ID NO: 7). One hundred ng of the luciferase-expressing plasmid vector pCMV-Gluc or 100 ng of the luciferase-expressing linear DNA was transfected using a FuGENE® HD Transfection Reagent kit (made by Roche) to 293 cells derived from human embryonic kidney cells. After 24 hours, the culture supernatant was collected, then the secreted luciferase contained in the culture supernatant was measured using a BioLux Gaussia Luciferase assay kit (made by New England Biolabs) and a GLOMAX 20/20 Luminometer (made by Promega); results of the measurement are shown in FIG. 8. Luciferase expression was extremely low with linear DNA using plasmid-derived poly(A). However, when an SV40 terminator sequence, a BGH terminator sequence, or a β-globin terminator sequence was used, luciferase gene expression using linear DNA increased and the linear DNA employing the BGH terminator sequence and the β-globin terminator sequence displayed gene expression beyond that of a plasmid vector. Of these, the linear DNA using the β-globin terminator sequence showed the highest luciferase gene expression.

Embodiment 2

(Search for Terminator Sequence Important to Gene Expression Using Linear DNA)

Figure 9:
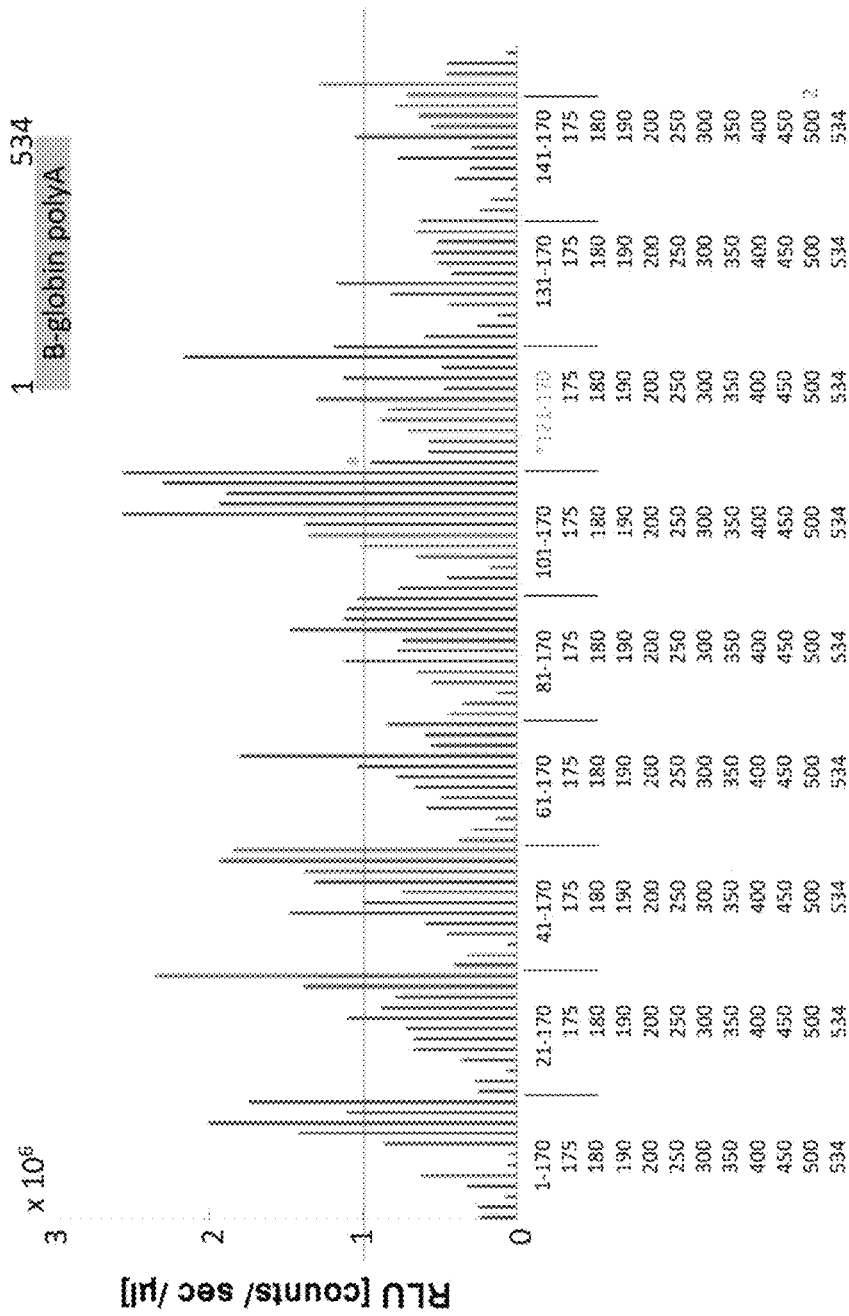
FIG. 9 illustrates results of a search for a β-globin terminator sequence having a length enabling engineering within a primer.

In order to quickly and easily produce linear DNA for gene expression, a terminator sequence is preferably as short as possible. In other words, a terminator sequence preferably has a length that enables the terminator sequence to bind downstream of a target RNA-expressing DNA sequence in one step and that is capable of being engineered within a primer. Under these circumstances, in order to investigate a terminator sequence that is as short as possible and that enables gene expression using linear DNA, a luciferase gene-expressing linear DNA was produced with the PCR method, the luciferase gene-expressing linear DNA including, in order, a CMV promoter, the secreted luciferase gene, and β-globin terminator sequences of various lengths shown in FIG. 9. One hundred ng of these luciferase-expressing linear DNAs were transfected to 293 cells using a FuGENE® HD Transfection Reagent kit (made by Roche), then the secreted luciferase contained in the culture supernatant collected after 24 hours was measured using a BioLux Gaussia Luciferase assay kit (made by New England Biolabs) and a GLOMAX 20/20 Luminometer (made by Promega) (FIG. 9). As a result, the β-globin terminator sequence of nucleobase numbers 121 to 170 (SEQ ID NO: 13) was determined to be the sequence that was shortest and capable of achieving the most efficient luciferase gene expression.

Figure 10:
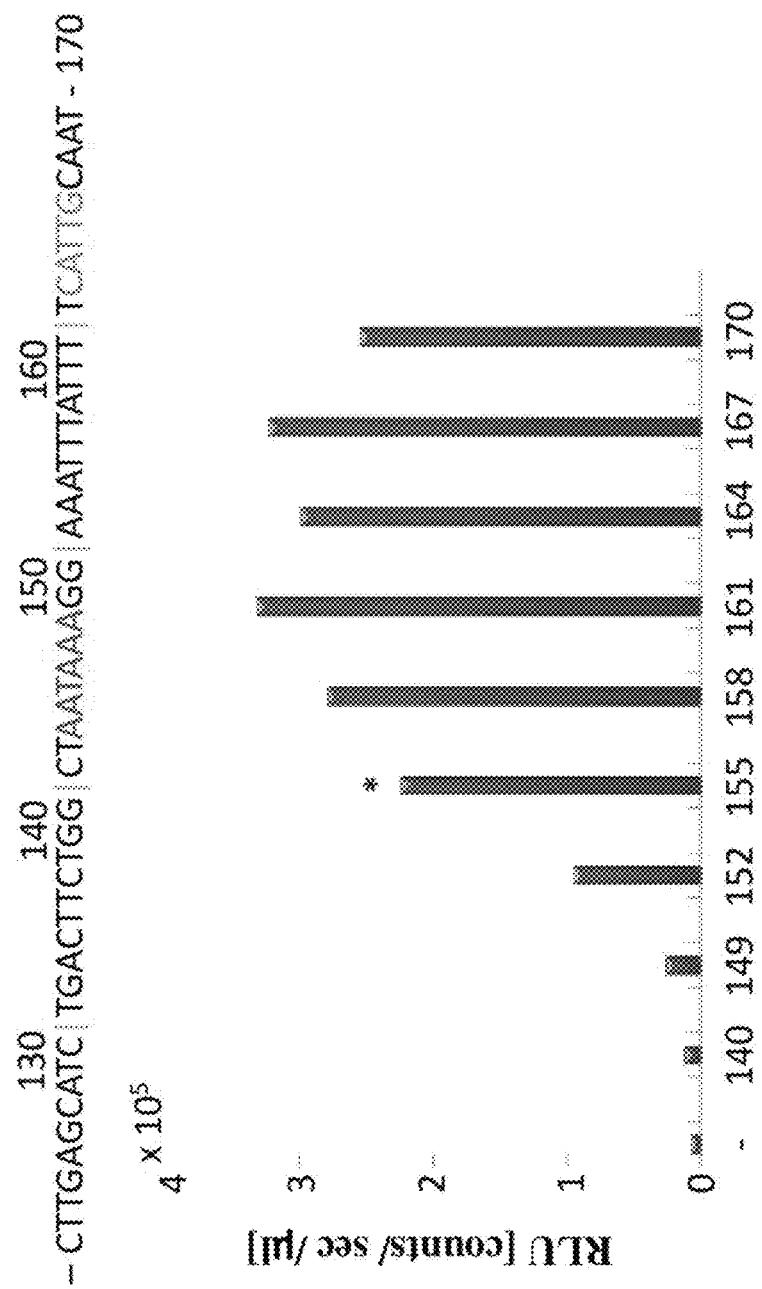
FIG. 10 illustrates that a sequence of nucleobase numbers 140 to 155 in the β-globin terminator sequence is important for a high level of protein expression using linear DNA. A graph illustrates, in order from the left, results of measuring an amount of secreted luciferase gene expression when using a negative control with no terminator sequence, and β-globin terminator sequences of nucleobase numbers 121 to 140, number 149, . . . , and number 170. The linear DNA using the β-globin terminator sequence having a length of nucleobase numbers 121 to 155 or more (indicated with an asterisk) showed a high amount of luceriferase gene expression. Figure discloses SEQ ID NO: 13.

Moreover, in order to discover the nucleobase important to gene expression in the β-globin terminator sequence of nucleobase numbers 121 to 170, a luciferase gene-expressing linear DNA was produced with the following method, the luciferase gene-expressing linear DNA binding the CMV promoter, the secreted luciferase gene, and the β-globin terminator sequences of various lengths, of nucleobase numbers 121 to 140, 149, 152, and 155 (SEQ ID NO: 14), 158 (SEQ ID NO: 15), 161 (SEQ ID NO: 16), 164 (SEQ ID NO: 17), 167 (SEQ ID NO: 18), or 170 (SEQ ID NO: 13). A linear DNA and CMV-hGluc-terminator(121-140)(b-globin) were produced on a template of pCMV-Gluc (made by New England Biolabs) with the PCR method using the primers shown in SEQ ID NOS: 4 and 19, the linear DNA including, in order, the CMV promoter, the secreted luciferase gene, and the β-globin terminator sequence of nucleobase numbers 121 to 140. The PCR reaction was performed using TOYOBO's KOD plus polymerase in adherence to the recommended protocol therefor. Final concentrations were adjusted to be, respectively, template: 50 pg/μL, forward primer: 0.3 μM, reverse primer: 0.3 μM, then cycles at 94° C. for 20 seconds, 55° C. for 30 seconds, and 68° C. for 2 minutes were carried out thirty times using an icycler thermal cycler (made by Bio-Rad). Using the CMV-hGluc-terminator(121-140)(b-globin) produced as the template, a luciferase-expressing linear DNA was produced using the PCR method by employing a forward primer shown in SEQ ID NO: 4 and reverse primers shown in 20 to 27, the luciferase-expressing linear DNA including, in order, the CMV promoter, the secreted luciferase gene, and the β-globin terminator sequences of various lengths. The PCR reaction was performed using KOD plus polymerase (made by Toyobo Co., Ltd.) in adherence to the recommended protocol therefor. Final concentrations were adjusted to be, respectively, template: 50 pg/μL, forward primer: 0.3 μM, reverse primer: 0.3 μM, then cycles at 94° C. for 20 seconds, 60° C. for 30 seconds, and 68° C. for 2 minutes were carried out thirty times using an icycler thermal cycler (made by Bio-Rad). One hundred ng each of these linear DNAs were transfected to 293 cells using a FuGENE® HD Transfection Reagent kit (made by Roche), then the secreted luciferase contained in the culture supernatant collected after 24 hours was measured using a BioLux Gaussia Luciferase assay kit (made by New England Biolabs) and a GLOMAX 20/20 Luminometer (made by Promega) (FIG. 10). As a result, with the β-globin terminator sequence of nucleobase numbers 121 to 140, luciferase gene expression was observed to a degree similar to that of the negative control linear DNA with no terminator. The β-globin terminator sequence of nucleobase numbers 121 to 155 and above displayed luciferase expression to a degree similar to that of the β-globin terminator sequence of nucleobase numbers 121 to 170. In addition, in a case where the β-globin terminator sequence of nucleobase numbers 121 to 152 was used, an amount of luciferase expression was low, suggesting that the β-globin terminator sequence of nucleobase numbers 155 to 170 is particularly important to gene expression using linear DNA.

Figure 11:
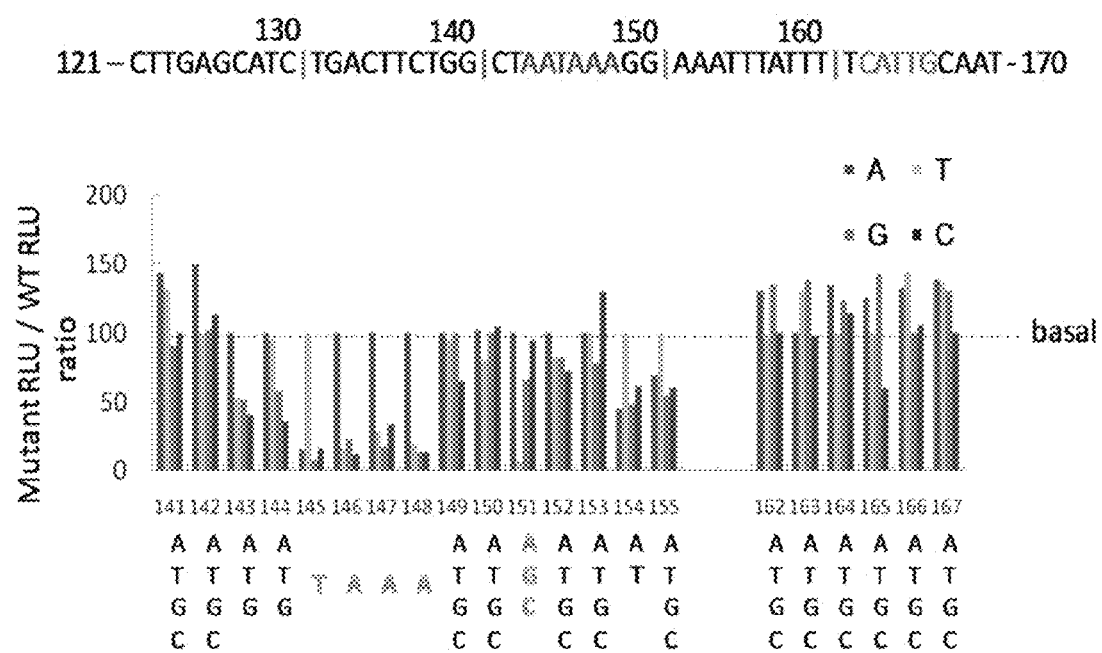
FIG. 11 shows that, of the β-globin terminator sequences, the sequence important to a high level of expression is (A/T/G), (A/T/G), T, A, A, A, (A/T/G/C), (A/T/G/C), (A/G/C). A graph illustrates results of measuring an amount of secreted luciferase gene expression using linear DNA that employs the above-noted terminator sequence for each of the nucleobases A, T, G, and C in the β-globin terminator sequence of nucleobase numbers 121 to 170. Numbers below the four-bar graphs indicate the nucleobase number of the substituted β-globin terminator sequence, and the four-bar graphs indicate cases where that nucleobase is, in order from the left, A, T, G, and C. The A, T, G, and C below the nucleobase number indicate a nucleobase capable of achieving gene expression to a degree similar to that of the linear DNA that employs a wild strain β-globin terminator sequence of nucleobase numbers 121 to 170. Figure discloses SEQ ID NOS 13 and 58, respectively, in order of appearance.

In order to investigate nucleobases important to gene expression using linear DNA, using the PCR method a linear DNA was produced having each nucleobase of a terminator sequence in a linear DNA substituted with adenine (A), thymine (T), guanine (G), or cytosine (C), the linear DNA undergoing substitution including, in order, the CMV promoter, the secreted luciferase gene, and the β-globin terminator sequence of nucleobase numbers 121 to 170 (SEQ ID NO: 13). A linear DNA and CMV-hGluc-terminator(121-140)(b-globin) were produced on a template of pCMV-Gluc (made by New England Biolabs) with the PCR method using the primers shown in SEQ ID NOS: 4 and 19, the linear DNA including, in order, the CMV promoter, the secreted luciferase gene, and the β-globin terminator sequence of nucleobase numbers 121 to 140. The PCR reaction was performed using KOD plus polymerase (made by Toyobo Co., Ltd.) in adherence to the recommended protocol therefor. Final concentrations were adjusted to be, respectively, template: 50 pg/μL, forward primer: 0.3 μM, reverse primer: 0.3 μM, then cycles at 94° C. for 20 seconds, 55° C. for 30 seconds, and 68° C. for 2 minutes were carried out thirty times using an icycler thermal cycler (made by Bio-Rad). Using the CMV-hGluc-terminator(121-140)(b-globin) produced as the template, a variant terminator linear DNA was produced with the PCR method by employing a forward primer shown in SEQ ID NO: 4 and a reverse primer that is a complementary sequence of a sequence in which each nucleobase 141 to 167 of the β-globin terminator sequence is substituted with adenine (A), thymine (T), guanine (G), or cytosine (C). One hundred ng each of these variant terminator linear DNAs were transfected to 293 cells using a FuGENE® HD Transfection Reagent kit (made by Roche), then the secreted luciferase contained in the culture supernatant collected after 24 hours was measured using a BioLux Gaussia Luciferase assay kit (made by New England Biolabs) and using a GLOMAX 20/20 Luminometer (made by Promega). An amount of luciferase expression in a case using linear DNA of a wild-type terminator sequence is treated as 100, and ratios relative thereto of luciferase expression in cases using the linear DNA of each variant terminator sequence are shown in FIG. 11. As a result, the β-globin terminator sequence of nucleobase numbers 143 to 148 and 151 is important, and the sequence of nucleobase numbers 143 to 151 in the β-globin terminator sequence (SEQ ID NO: 7) is a sequence of nine connected nucleobases (A/T/G), (A/T/G), T, A, A, A, (A/T/G/C), (A/T/G/C), (A/G/C), suggesting that this is important to gene expression using the linear DNA.

Embodiment 3

(Consideration of Terminator Sequence Sources and Types of Cells)

A review was made of types of terminator sequences, types of target cells, and binding of nine nucleobases between a target RNA-expressing DNA sequence and the terminator as they concern gene expression using linear DNA.

A linear DNA was produced with the following method, the linear DNA including, in order, the CMV promoter, the secreted luciferase gene, and the β-globin terminator sequence of nucleobase numbers 121 to 140, 121 to 155 (SEQ ID NO: 14), 121 to 160 (SEQ ID NO: 28), 121 to 170 (SEQ ID NO: 13), 121 to 180 (SEQ ID NO: 29), 121 to 190 (SEQ ID NO: 30), 121 to 200 (SEQ ID NO: 31), or 121 to 220 (SEQ ID NO: 1). A linear DNA and CMV-hGluc-terminator(121-140)(b-globin) were produced on a template of pCMV-Gluc (made by New England Biolabs) with the PCR method using the primers shown in SEQ ID NOS: 4 and 19, the linear DNA including, in order, the CMV promoter, the secreted luciferase gene, and the β-globin terminator sequence of nucleobase numbers 121 to 140. The PCR reaction was performed using KOD plus polymerase (made by Toyobo Co., Ltd.) in adherence to the recommended protocol therefor. Final concentrations were adjusted to be, respectively, template: 50 pg/μL, forward primer: 0.3 μM, reverse primer: 0.3 μM, then cycles at 94° C. for 20 seconds, 55° C. for 30 seconds, and 68° C. for 2 minutes were carried out thirty times using an icycler thermal cycler (made by Bio-Rad). Using the CMV-hGluc-terminator(121-140)(b-globin) produced as the template, a luciferase-expressing linear DNA was produced using the PCR method by employing a forward primer shown in SEQ ID NO: 4 and primers shown in SEQ ID NOS: 22, 32, 27, and 33 to 36, the luciferase-expressing linear DNA including, in order, the CMV promoter, the secreted luciferase gene, and the β-globin terminator sequences of various lengths. The PCR reaction was performed using KOD plus polymerase (made by Toyobo Co., Ltd.) in adherence to the recommended protocol therefor. Final concentrations were adjusted to be, respectively, template: 50 pg/μL, forward primer: 0.3 μM, reverse primer: 0.3 μM, then cycles at 94° C. for 20 seconds, 60° C. for 30 seconds, and 68° C. for 2 minutes were carried out thirty times using an icycler thermal cycler (made by Bio-Rad). A β-globin terminator nucleobase sequence 121 to 155 (151T) of numbers 121 to 155 had the nucleobase of nucleobase number 151 substituted with thymine (T), nucleobase number 151 corresponding to the ninth nucleobase of the nine connected nucleobases (A/T/G), (A/T/G), T, A, A, A, (A/T/G/C), (A/T/G/C), (A/G/C) which are important to gene expression using linear DNA. The β-globin terminator nucleobase sequence 121 to 155 (151T) was the negative control, which was produced in the same manner using a primer of a terminator sequence containing a variant.

In addition, a linear DNA was produced with the following method, the linear DNA including, in order, the CMV promoter, the secreted luciferase gene, and an SV40 terminator nucleobase sequence of nucleobase numbers 121 to 140 or 121 to 220 (SEQ ID NO: 2). A linear DNA and CMV-hGluc-terminator(121-140)(SV40) were produced on a template of pCMV-Gluc (made by New England Biolabs) with the PCR method using the primers shown in SEQ ID NOS: 4 and 37, the linear DNA including, in order, the CMV promoter, the secreted luciferase gene, and the SV40 terminator sequence of nucleobase numbers 121 to 140. The PCR reaction was performed using KOD plus polymerase (made by Toyobo Co., Ltd.) in adherence to the recommended protocol therefor. Final concentrations were adjusted to be, respectively, template: 50 pg/μL, forward primer: 0.3 μM, reverse primer: 0.3 μM, then cycles at 94° C. for 20 seconds, 55° C. for 30 seconds, and 68° C. for 2 minutes were carried out thirty times using an icycler thermal cycler (made by Bio-Rad). Using the CMV-hGluc-terminator(121-140)(SV40) produced as the template, a luciferase-expressing linear DNA and CMV-hGluc-SV40pA121-220 were produced using the PCR method by employing primers shown in SEQ ID NOS: 4 and 38, the luciferase-expressing linear DNA including, in order, the CMV promoter, the secreted luciferase gene, and the SV40 terminator sequence of nucleobase numbers 121 to 220. The PCR reaction was performed using KOD plus polymerase (made by Toyobo Co., Ltd.) in adherence to the recommended protocol therefor. Final concentrations were adjusted to be, respectively, template: 50 pg/μL, forward primer: 0.3 μM, reverse primer: 0.3 μM, then cycles at 94° C. for 20 seconds, 60° C. for 30 seconds, and 68° C. for 2 minutes were carried out thirty times using an icycler thermal cycler (made by Bio-Rad). The linear DNA and a 121-220 AATAAA mutation are the negative control, the linear DNA including, in order, the CMV promoter, the secreted luciferase gene, and the SV40 terminator sequence of nucleobase numbers 121 to 220 shown in SEQ ID NO: 39 and having a variant transfected with AATAAA. The negative control was produced in the same manner using a primer of the terminator sequence that includes the variant. The AATAAA corresponds to the first six nucleobases of the nine connected nucleobases (A/T/G), (A/T/G), T, A, A, A, (A/T/G/C), (A/T/G/C), (A/G/C) that are important to gene expression using linear DNA. A luciferase-expressing plasmid vector pCMV-Gluc, a linear DNA, and CMV-Glucliner were used as a control, the linear DNA being amplified on a template of the aforementioned plasmid with the PCR method by employing primers shown in SEQ ID NOS: 4 and 12, and the linear DNA including a CMV promoter, a luciferase gene, and a plasmid poly(A).

Further, a linear DNA was produced having an annealed sequence with approximately nine excess nucleobases bound between a target RNA-expressing DNA sequence and a terminator, then the gene expression thereof was investigated. Using GGGCCCGGG (SEQ ID NO: 51) as the annealed sequence, the linear DNA was produced with the following method. First, a linear DNA and CMV-hGluc-3GC9 were produced on a template of pCMV-Gluc (made by New England Biolabs) with the PCR method using the primers shown in SEQ ID NOS: 4 and 47, the linear DNA including, in order, the CMV promoter, the secreted luciferase gene, and the annealed sequence (SEQ ID NO: 51). The PCR reaction was performed using KOD plus polymerase (made by Toyobo Co., Ltd.) in adherence to the recommended protocol therefor. Final concentrations were adjusted to be, respectively, template: 50 pg/µL, forward primer: 0.3 µM, reverse primer: 0.3 µM, then cycles at 94° C. for 20 seconds, 55° C. for 30 seconds, and 68° C. for 2 minutes were carried out thirty times using an icycler thermal cycler (made by Bio-Rad). Using the CMV-hGluc-3GC9 produced as the template, a luciferase-expressing linear DNA and a linear DNA CMV-hGluc-3GC9-terminator were produced using the PCR method by employing the primers shown in SEQ ID NOS: 4 and 48 to 50, the luciferase-expressing linear DNA including, in order, the CMV promoter, the secreted luciferase gene, the annealed sequence (SEQ ID NO: 51), and the terminator sequence, while the linear DNA CMV-hGluc-3GC9-terminator included, in order, the CMV promoter, the secreted luciferase gene, the nine nucleobases of the annealed sequence (GGGCCCGGG; SEQ ID NO: 51), the β-globin terminator sequence of nucleobase numbers 121 to 190 (SEQ ID NO: 30), the β-globin terminator sequence of nucleobase numbers 130 to 190, or the SV40 terminator sequence of numbers 130 to 220. The PCR reaction was performed using KOD plus polymerase (made by Toyobo Co., Ltd.) in adherence to the recommended protocol therefor. Final concentrations were adjusted to be, respectively, template: 50 pg/µL, forward primer: 0.3 µM, reverse primer: 0.3 µM, then cycles at 94° C. for 20 seconds, 60° C. for 30 seconds, and 68° C. for 2 minutes were carried out thirty times using an icycler thermal cycler (made by Bio-Rad).

Figure 12:
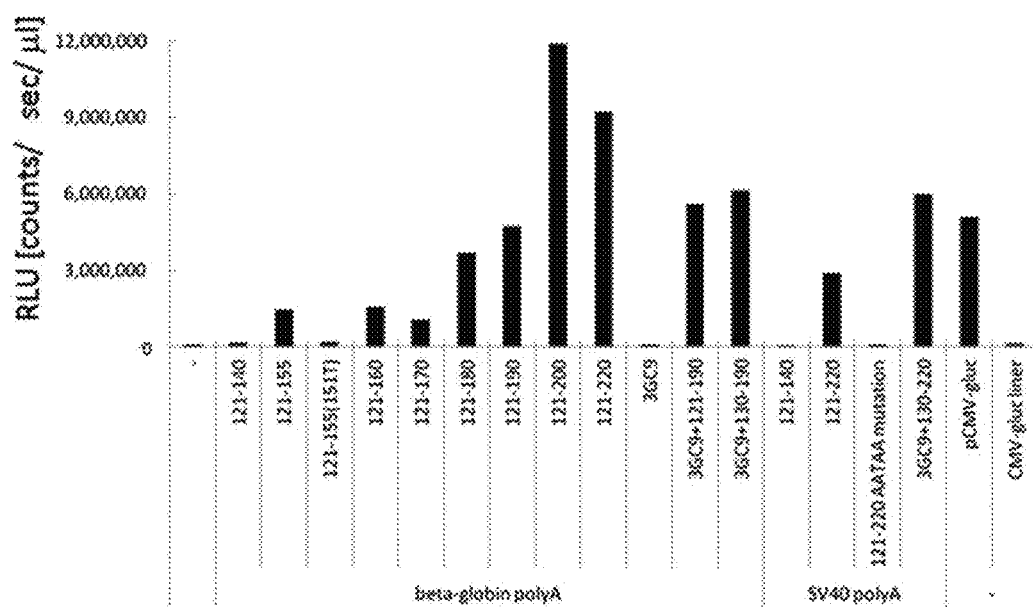
FIG. 12 illustrates that a high level of gene expression was obtained in human embryonic kidney cell-derived 293 cells using a linear DNA that includes, in order, a CMV promoter, a secreted luciferase gene, and a β-globin terminator sequence of nucleobase numbers 121 to 200 or an SV40 terminator sequence of nucleobase numbers 121 to 220.
Figure 13:
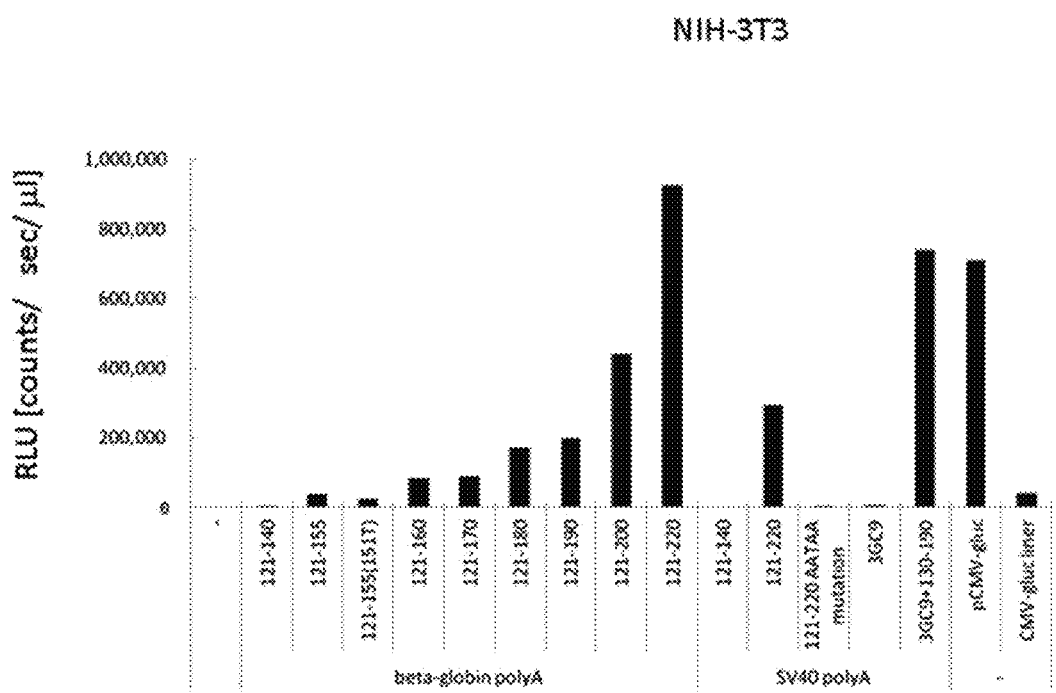
FIG. 13 illustrates that a high level of gene expression was obtained in mouse fibroblast NIH-3T3 cells using a linear DNA that includes, in order, a CMV promoter, a secreted luciferase gene, and a β-globin terminator sequence of nucleobase numbers 121 to 220 or an SV40 terminator nucleobase sequence of nucleobase numbers 121 to 220.
Figure 14:
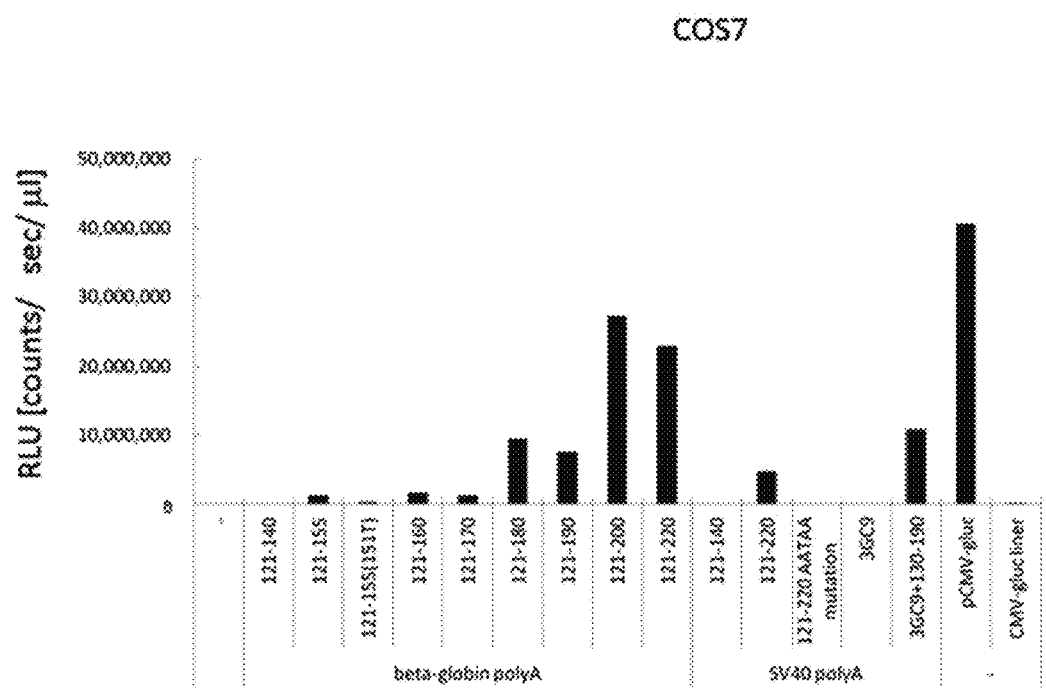
FIG. 14 illustrates that a high level of gene expression was obtained in COS7 cells derived from African green monkey kidney using a linear DNA that includes, in order, a CMV promoter, a secreted luciferase gene, and a β-globin terminator sequence of nucleobase numbers 121 to 200 or an SV40 terminator sequence of nucleobase numbers 121 to 220.
Figure 15:
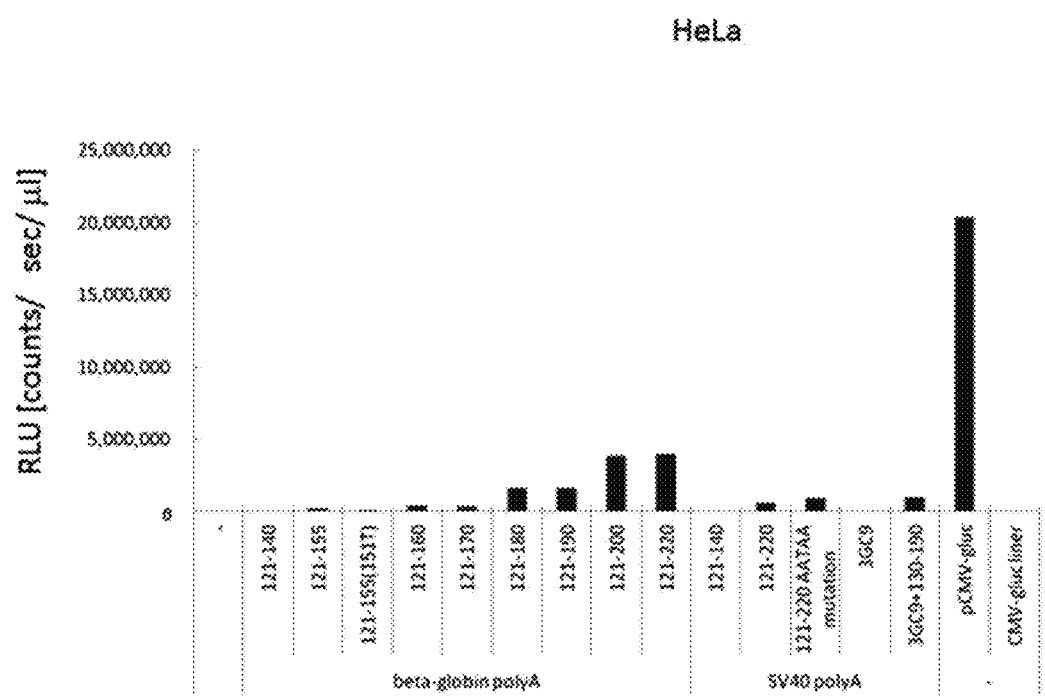
FIG. 15 illustrates that a high level of gene expression was obtained in human epithelial cell-derived HeLa cells using a linear DNA that includes, in order, a CMV promoter, a secreted luciferase gene, and a β-globin terminator sequence of nucleobase numbers 121 to 200 and 121 to 220 or an SV40 terminator sequence of nucleobase numbers 121 to 220.
Figure 16:
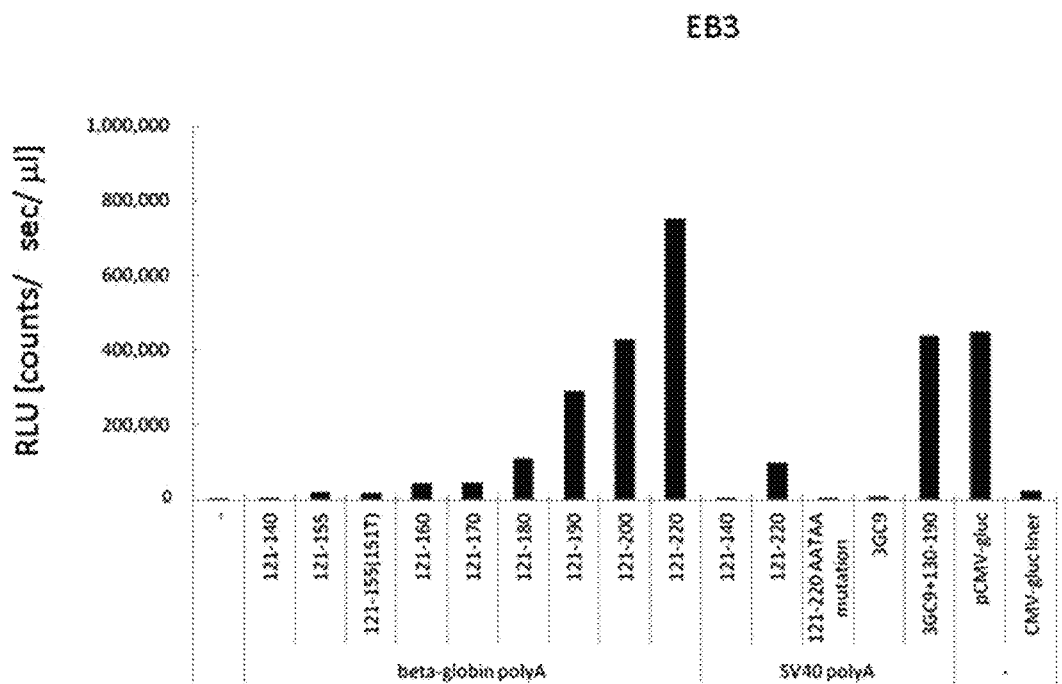
FIG. 16 illustrates that a high level of gene expression was obtained in EB3 cells (mouse ES cells) using a linear DNA that includes, in order, a CMV promoter, a secreted luciferase gene, and a β-globin terminator sequence of nucleobase numbers 121 to 220 or an SV40 terminator nucleobase sequence of nucleobase numbers 121 to 220.

The linear DNAs produced were, respectively, transfected using a FuGENE® HD Transfection Reagent kit (made by Roche) to human embryonic kidney 293 cells, to mouse fibroblast NIH-3T3 cells, to COS7 cells derived from African green monkey kidney, to HeLa cells derived from human epithelial cells, or to EB3 cells (mouse ES cells). Using 15 µL of culture supernatant collected after 24 hours, an amount of secreted luciferase was measured by a GLO-MAX 20/20 Luminometer (made by Promega) using a BioLux Gaussia Luciferase assay kit (made by New England Biolabs). Based on a measured value for a measurement time of three seconds, the amount of luciferase is shown in FIGS. 12 to 14 as a measured value for a measured culture supernatant of 1 µL and a measurement time of around one second. In 293 cells (FIG. 12), NIH-3T3 cells (FIG. 13), and EB3 cells (FIG. 16), higher luciferase gene expression was observed in linear DNA using a β-globin terminator sequence than in a plasmid vector. In COS7 cells (FIG. 14) and HeLa cells (FIG. 15), the plasmid vector showed a luciferase gene expression higher even than the linear DNA using the β-globin terminator sequence. However, the linear DNA using the β-globin terminator sequence of nucleobase numbers 121 to 220 showed a sufficiently high expression as compared to the negative control of 121 to 155 (151T) and was shown to be useful. In addition, of the linear DNAs used, the highest luciferase expression for the 293 cells (FIG. 12), the COS7 cells (FIG. 14), and the HeLa cells (FIG. 15) was observed in the β-globin terminator nucleobase sequence of numbers 121 to 200, and the highest luciferase expression for the NIH-3T3 cells (FIG. 13) and the EB3 cells (FIG. 16) was observed in the β-globin terminator nucleobase sequence of nucleobase numbers 121 to 220. Further, in any of the kinds of cells, using the β-globin terminator sequence gave a higher level of gene expression than using the SV40 terminator sequence. Nevertheless, because sufficiently high gene expression was shown by the negative control (the SV40 terminator sequence 121-220 AATAAA mutation) in the 293 cells (FIG. 12), NIH-3T3 cells (FIG. 13), COS7 cells (FIG. 14), and EB3 cells (FIG. 16), use of the SV40 terminator sequence of nucleobase numbers 121 to 220 in gene expression in mammalian cells with linear DNA was also shown to be possible. In the SV40 terminator sequence of nucleobase numbers 121 to 220, AAcgAA was substituted for AATAAA in two locations, and the SV40 terminator sequence 121-220 AATAAA mutation using this variant terminator sequence (SEQ ID NO: 39) had greatly reduced gene expression. Therefore, even when the terminator sequence is long, the β-globin terminator sequence of nucleobase numbers 143 to 151 having the sequence of nine connected nucleobases (A/T/G), (A/T/G), T, A, A, A, (A/T/G/C), (A/T/G/C), (A/G/C) is shown to be important for gene expression using linear DNA. In addition, even in linear DNA having the nine nucleobases (SEQ ID NO: 51) bound between the target RNA-expressing DNA sequence and the terminator, the same level of gene expression was displayed as that of a linear DNA not having the nine nucleobases bound thereto, thus suggesting that decreased expression due to binding the annealed sequence of about nine nucleobases between the target RNA-expressing DNA sequence and the terminator does not occur. Accordingly, a target RNA-expressing DNA sequence having an annealed sequence on the C-terminus is used as the template, the target RNA-expressing DNA sequence being amplified with the PCR method using a reverse primer for amplification of a target RNA-expressing DNA sequence that includes an annealed sequence of about nine nucleobases on the N-terminus. When the target RNA-expressing DNA sequence having the annealed sequence on the C-terminus is used as the template, a complementary sequence of the terminator sequence that includes the annealed sequence on the C-terminus can be used as the reverse primer for binding the common terminator sequence, and thus linear DNA for gene expression that includes various kinds of terminator sequences can be readily produced at a low cost. Moreover, an amount of RNA expression within the cells can be controlled by using linear DNA that employs various lengths and kinds of terminator sequences, which is particularly useful in a case where a gene or the like expected to display poisonous properties with respect to the cell is to be expressed, for example.

Embodiment 4

(Consideration of Promoters)

Figure 17:
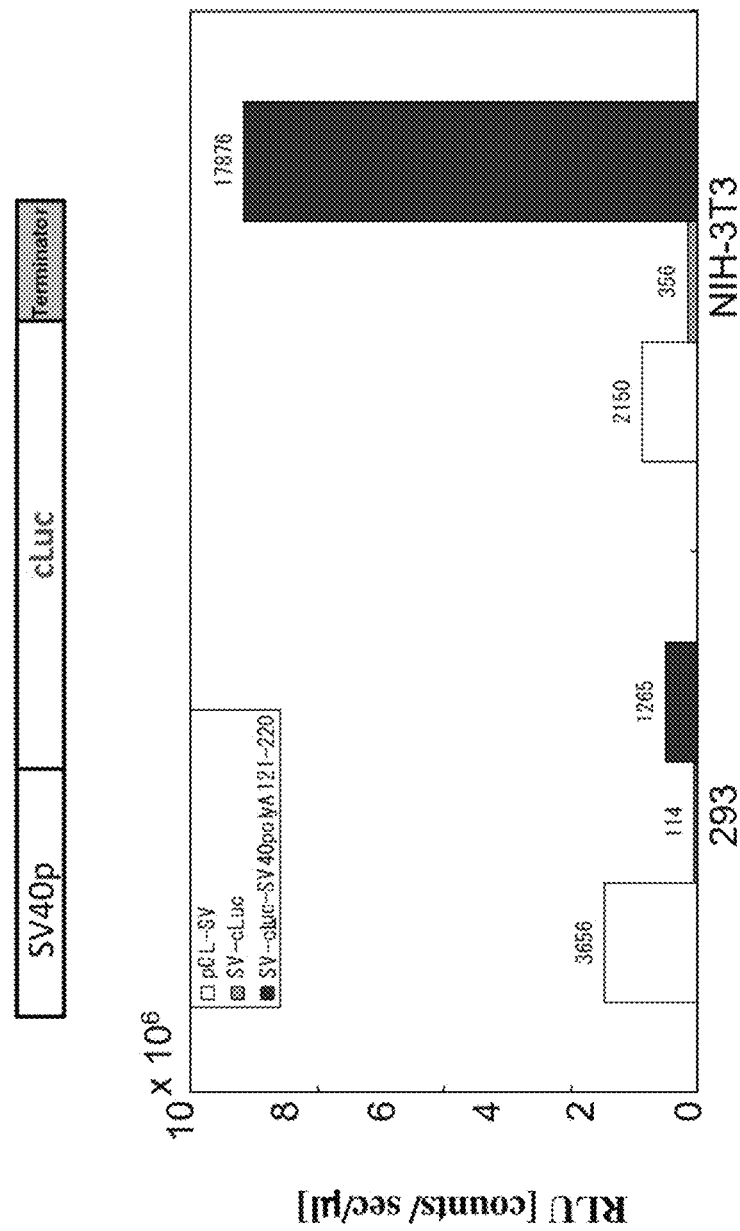
FIG. 17 shows luciferase gene expression in human embryonic kidney cell-derived 293 cells and mouse fibroblast NIH-3T3 cells using a linear DNA having an SV40 promoter sequence and an SV40 terminator sequence of nucleobase numbers 121 to 220. pCL-SV indicates that a secreted luciferase gene-expressing linear plasmid vector was used. SV-cLuc indicates that a secreted luciferase gene-expressing linear DNA having the SV40 promoter sequence and a plasmid vector-derived terminator sequence was used. SV-cLucSV40poly(A)121-220 indicates that a secreted luciferase gene-expressing linear DNA having the SV40 promoter sequence and having the SV40 terminator sequence of nucleobase numbers 121 to 220 was used.

A linear DNA and SV-cLuc-SV40polyA121-220 were produced with the following method, the linear DNA including, in order, the SV40 promoter, the secreted luciferase gene, and the SV40 terminator sequence of nucleobase numbers 121 to 220. A linear DNA and SV40-hCluc-terminator(121-140)(SV40) were produced using the primers shown in SEQ ID NOS: 52 and 53 with pCL-SV (made by ATTO Corporation) as a template, the linear DNA including, in order, the SV40 promoter, the secreted luciferase gene, and the SV40 terminator sequence of nucleobase numbers 121 to 140. The PCR reaction was performed using KOD plus polymerase (made by Toyobo Co., Ltd.) in adherence to the recommended protocol therefor. Final concentrations were adjusted to be, respectively, template: 50 pg/µL, forward primer: 0.3 µM, reverse primer: 0.3 µM, then cycles at 94° C. for 20 seconds, 55° C. for 30 seconds, and 68° C. for 2 minutes were carried out thirty times using an icycler thermal cycler (made by Bio-Rad). Using the SV40-hCluc-terminator(121-140)(SV40) produced as the template, a luciferase-expressing linear DNA and SV40-hCluc-SV40pA121-220 were produced using the PCR method by employing the primers shown in SEQ ID NOS: 52 and 38, the luciferase-expressing linear DNA including, in order, the SV40 promoter, the secreted luciferase gene, and the SV40 terminator sequence of nucleobase numbers 121 to 220. The PCR reaction was performed using KOD plus polymerase (made by Toyobo Co., Ltd.) in adherence to the recommended protocol therefor. Final concentrations were adjusted to be, respectively, template: 50 pg/μL, forward primer: 0.3 μM, reverse primer: 0.3 μM, then cycles at 94° C. for 20 seconds, 60° C. for 30 seconds, and 68° C. for 2 minutes were carried out thirty times using an icycler thermal cycler (made by Bio-Rad). A linear DNA and SV-cLuc were used as a control, the linear DNA being produced on a template of pCL-SV with the PCR method and including, in order, the SV40 promoter, the secreted luciferase gene, and the plasmid poly(A). One hundred ng each of these linear DNAs was transfected to 293 cells or NIH-3T3 cells using a FuGENE® HD Transfection Reagent kit (made by Roche), then the secreted luciferase contained in the culture supernatant collected after 24 hours was measured using a CLuc Reporter Assay Kit (made by ATTO Corporation) and a GLOMAX 20/20 Luminometer (made by Promega) (FIG. 17). As a result, the linear DNA using the SV40 promoter and the SV40 terminator sequence of nucleobase numbers 121 to 220 was also capable of expressing the luciferase gene in 293 cells and NIH-3T3 cells, and a level of gene expression was observed in the NIH-3T3 cells higher even than in a case using the plasmid vector.

As a result of the above, in a case where the SV40 promoter was used, luciferase gene expression was confirmed to be possible in 293 cells and NIH-3T3 cells by using linear DNA. In other words, the linear DNA of the present invention was shown to be capable of gene expression in various kinds of mammalian cells using promoters or terminator sequences from a variety of sources.

Embodiment 5

(Production of Linear DNA)

An example of producing linear DNA is given below.

1. Case when a construct is present in which the target RNA-expressing DNA sequence is already connected downstream of the targeted promoter and the terminator sequence is bound in one step (see FIG. 2, left panel):

An example is given below of CMV-hGluc-terminator (β-globin).

Figure 18:
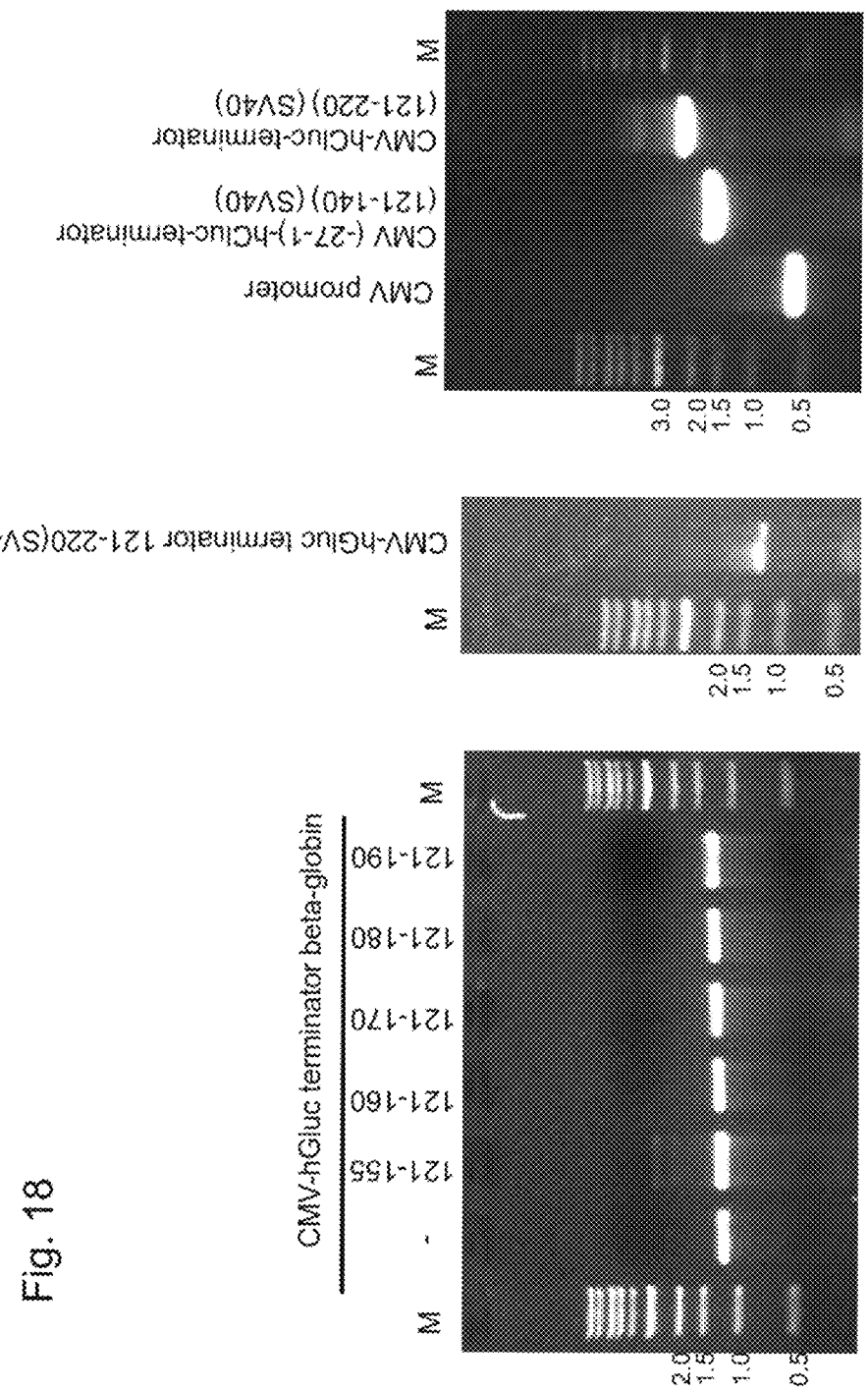
FIG. 18 shows results of agarose electrophoresis of the produced linear DNA for gene expression. M indicates a marker (kbp). A left panel shows CMV-hGluc terminator beta-globin linear DNA with no terminator sequence and using β-globin terminator sequences of nucleobase numbers 121 to 155, 121 to 160, 121 to 170, 121 to 180, and 121 to 190. A middle panel shows CMV-hGluc terminator 121-220 (SV40) linear DNA. A right panel shows a CMV promoter, CMV(–27-1)-hCluc-terminator(121-140)(SV40), and CMV-hCluc-terminator(121-220)(SV40) linear DNA.

A linear DNA was produced on a template of pCMV-Gluc (made by New England Biolabs) with the PCR method using the primers shown in SEQ ID NOS: 4 and 22 and 32 to 34, the linear DNA including, in order, the CMV promoter, the secreted luciferase gene, and the β-globin terminator sequence. The β-globin terminator sequence of the linear DNA included, in order, the β-globin terminator sequences of nucleobase numbers 121 to 155, 121 to 160, 121 to 180, and 121 to 190. The PCR reaction was performed using KOD plus polymerase (made by Toyobo Co., Ltd.) in adherence to the recommended protocol therefor. Final concentrations were adjusted to be, respectively, template: 50 pg/μL, forward primer: 0.3 μM, reverse primer: 0.3 μM, then cycles at 94° C. for 20 seconds, 55° C. for 30 seconds, and 68° C. for 2 minutes were carried out thirty times using an icycler thermal cycler (made by Bio-Rad). The linear DNA produced was confirmed with agarose electrophoresis, the results of which are shown in a left panel of FIG. 18.

2. Case 2-1 when a construct is present in which the target RNA-expressing DNA sequence is already connected downstream of the targeted promoter and the terminator sequence is bound in two steps:

An example is given below of CMV-hGluc-terminator (SV40). (See FIG. 2, right panel.)

A linear DNA and CMV-hGluc-terminator(121-140) (SV40) were produced on a template of pCMV-Gluc (made by New England Biolabs) with the PCR method using the primers shown in SEQ ID NOS: 4 and 37, the linear DNA including, in order, the CMV promoter, the secreted luciferase gene, and the SV40 terminator sequence of nucleobase numbers 121 to 140. The PCR reaction was performed using KOD plus polymerase (made by Toyobo Co., Ltd.) in adherence to the recommended protocol therefor. Final concentrations were adjusted to be, respectively, template: 50 pg/μL, forward primer: 0.3 μM, reverse primer: 0.3 μM, then cycles at 94° C. for 20 seconds, 55° C. for 30 seconds, and 68° C. for 2 minutes were carried out thirty times using an icycler thermal cycler (made by Bio-Rad). Using the CMV-hGluc-terminator(121-140)(SV40) produced as the template, a luciferase-expressing linear DNA and CMV-hGluc-SV40pA121-220 were produced using the PCR method by employing the primers shown in SEQ ID NOS: 4 and 38, the luciferase-expressing linear DNA including, in order, the CMV promoter, the secreted luciferase gene, and the SV40 terminator sequence of nucleobase numbers 121 to 220 (length: one hundred nucleobases). The PCR reaction performed cycles at 94° C. for 20 seconds, 60° C. for 30 seconds, and 68° C. for 2 minutes thirty times with the above-noted and a reaction solution composition. The linear DNA produced was confirmed with agarose electrophoresis, the results of which are shown in a center panel of FIG. 18.

2-2. CMV-EGFP-terminator(SV40) (See FIG. 2, right panel)

A linear DNA was produced with the following method, the linear DNA including, in order, the CMV promoter, the EGFP, and the SV40 terminator sequence. A linear DNA and CMV-EGFP-terminator(121-140) were produced on a template of pEGFP-C1 (made by Clontech) with the PCR method using the primers shown in SEQ ID NOS: 4 and 44, the linear DNA including, in order, the CMV promoter, the secreted luciferase gene, and the SV40 terminator sequence of nucleobase numbers 121 to 140. The PCR reaction was performed using KOD plus polymerase (made by Toyobo Co., Ltd.) in adherence to the recommended protocol therefor. Final concentrations were adjusted to be, respectively, template: 50 pg/μL, forward primer: 0.3 μM, reverse primer: 0.3 μM, then cycles at 94° C. for 20 seconds, 55° C. for 30 seconds, and 68° C. for 2 minutes were carried out thirty times using an icycler thermal cycler (made by Bio-Rad). With this as a template, a linear DNA and CMV-EGFP-SV40pA121-220 were produced with the PCR method using the primers shown in SEQ ID NOS: 4 and 38, the linear DNA including, in order, the CMV promoter, the secreted luciferase gene, and the SV40 terminator sequence of nucleobase numbers 121 to 220. The PCR reaction performed cycles at 94° C. for 20 seconds, 60° C. for 30 seconds, and 68° C. for 2 minutes thirty times with the above-noted and a reaction solution composition.

3. Case when no construct is present in which the target RNA-expressing DNA sequence is connected downstream of the targeted promoter and the terminator sequence is bound in two steps:

3-2. CMV-hCluc-terminator(β-globin) (See FIG. 4, left panel)

A linear DNA was produced with the following method, the linear DNA including, in order, the CMV promoter, hCluc, and the β-globin terminator sequence. The CMV promoter was amplified on a template of pEGFP-C1 (made by Clontech) with the PCR method using the primers shown in SEQ ID NOS: 4 and 6. A linear DNA and CMV(-27-1)-hCluc-terminator(121-140)(b-globin) were produced on a template of pCL-SV (made by ATTO Corporation) with the PCR method using the primers shown in SEQ ID NOS: 41 and 42, the linear DNA including, in order, a sequence of a region on a C-terminus side of the CMV promoter, the secreted luciferase gene, and the β-globin terminator sequence of nucleobase numbers 121 to 140. The PCR reaction was performed using KOD plus polymerase (made by Toyobo Co., Ltd.) in adherence to the recommended protocol therefor. Final concentrations were adjusted to be, respectively, template: 50 pg/μL, forward primer: 0.3 μM, reverse primer: 0.3 μM, then cycles at 94° C. for 20 seconds, 55° C. for 30 seconds, and 68° C. for 2 minutes were carried out thirty times using an icycler thermal cycler (made by Bio-Rad). Next, using the CMV promoter and the CMV(-27-1)-hCluc-terminator(121-140)(b-globin) produced as the template, a linear DNA and CMV-hCluc-bglobinpA121-220 were produced using the PCR method by employing the primers shown in SEQ ID NOS: 4, and 35 and 36, the linear DNA including, in order, the CMV promoter, the secreted luciferase gene, and the SV40 terminator sequence of nucleobase numbers 121 to 200 and 121 to 220. The PCR reaction performed cycles at 94° C. for 20 seconds, 60° C. for 30 seconds, and 68° C. for 2 minutes thirty times with the above-noted and a reaction solution composition.

3-3. CMV-hCluc-terminator(SV40) (See FIG. 4, left panel)

A linear DNA was produced with the following method, the linear DNA including, in order, the CMV promoter, the hCluc, and the SV40 terminator sequence. The CMV promoter was amplified on a template of pEGFP-C1 (made by Clontech) with the PCR method using the primers shown in SEQ ID NOS: 4 and 6. In addition, a linear DNA and CMV(-27-1)-hCluc-terminator(121-140)(SV40) were produced on a template of pCL-SV (made by ATTO Corporation) with the PCR method using the primers shown in SEQ ID NOS: 41 and 43, the linear DNA including, in order, a sequence of a region on a C-terminus side of the CMV promoter, the secreted luciferase gene, and the SV40 terminator sequence of nucleobase numbers 121 to 140. The PCR reaction was performed using KOD plus polymerase (made by Toyobo Co., Ltd.) in adherence to the recommended protocol therefor. Final concentrations were adjusted to be, respectively, template: 50 pg/μL, forward primer: 0.3 μM, reverse primer: 0.3 μM, then cycles at 94° C. for 20 seconds, 55° C. for 30 seconds, and 68° C. for 2 minutes were carried out thirty times using an icycler thermal cycler (made by Bio-Rad). Next, using the CMV promoter and the CMV(-27-1)-hCluc-terminator(121-140)(SV40) as the template, a linear DNA and CMV-hCluc-terminator(121-220)(SV40) were produced using the PCR method by employing the primers shown in SEQ ID NOS: 4 and 38, the linear DNA including, in order, the CMV promoter, the secreted luciferase gene, and the SV40 terminator sequence of nucleobase numbers 121 to 220. The PCR reaction performed cycles at 94° C. for 20 seconds, 60° C. for 30 seconds, and 68° C. for 2 minutes thirty times with the above-noted and a reaction solution composition. The linear DNA produced was confirmed with agarose electrophoresis, the results of which are shown in a right panel of FIG. 18.

3-4. CMV-hGluc-terminator(β-globin) (See FIG. 4, right panel)

A linear DNA was produced with the following method, the linear DNA including, in order, the CMV promoter, hGluc, and the β-globin terminator sequence. The CMV promoter was amplified on a template of pEGFP-C1 (made by Clontech) with the PCR method using the primers shown in SEQ ID NOS: 4 and 6. In addition, a linear DNA and CMV(-27-1)-hGluc-terminator(121-140)(b-globin) were produced on a template of pCMV-Gluc (made by New England Biolabs) with the PCR method using the primers shown in SEQ ID NOS: 40 and 19, the linear DNA including, in order, a sequence of a region on a C-terminus side of the CMV promoter, the secreted luciferase gene, and the β-globin terminator sequence of nucleobase numbers 121 to 140. The PCR reaction was performed using KOD plus polymerase (made by Toyobo Co., Ltd.) in adherence to the recommended protocol therefor. Final concentrations were adjusted to be, respectively, template: 50 pg/μL, forward primer: 0.3 μM, reverse primer: 0.3 μM, then cycles at 94° C. for 20 seconds, 55° C. for 30 seconds, and 68° C. for 2 minutes were carried out thirty times using an icycler thermal cycler (made by Bio-Rad). Using the CMV promoter and the CMV(-27-1)-hGluc-terminator(121-140)(b-globin) produced as the template, a luciferase-expressing linear DNA was produced using the PCR method by employing a forward primer shown in SEQ ID NO: 4 and a reverse primer shown in 36, the luciferase-expressing linear DNA including, in order, the CMV promoter, the secreted luciferase gene, and the β-globin terminator sequence of nucleobase sequence 121 to 220. The PCR reaction performed cycles at 94° C. for 20 seconds, 60° C. for 30 seconds, and 68° C. for 2 minutes thirty times with the above-noted and a reaction solution composition.

3-5. SV40-hGluc-terminator(SV40) (See FIG. 4, right panel)

A linear DNA was produced with the following method, the linear DNA including, in order, the SV40 promoter, hGluc, and the SV40 terminator sequence. A linear DNA and SV40-hGluc(1-30) were produced on a template of pEGFP-C1 (made by Clontech) with the PCR method using the primers shown in SEQ ID NOS: 3 and 45, the linear DNA including, in order, the SV40 promoter and the secreted luciferase gene of nucleobase numbers 1 to 30. A linear DNA and hGluc-terminator(121-140) were produced with the PCR method using the primers shown in SEQ ID NOS: 19 and 46, the linear DNA including, in order, the secreted luciferase gene and the β-globin terminator sequence of nucleobase numbers 121 to 140. The PCR reaction was performed using KOD plus polymerase (made by Toyobo Co., Ltd.) in adherence to the recommended protocol therefor. Final concentrations were adjusted to be, respectively, template: 50 pg/μL, forward primer: 0.3 μM, reverse primer: 0.3 μM, then cycles at 94° C. for 20 seconds, 55° C. for 30 seconds, and 68° C. for 2 minutes were carried out thirty times using an icycler thermal cycler (made by Bio-Rad). Next, using the SV40-hGluc(1-30) and the hGluc-terminator (121-140) as the template, a linear DNA and an SV40-hGluc-bglobinpA121-200 were produced using the PCR method by employing the primers shown in SEQ ID NOS: 3 and 36, the linear DNA including, in order, the SV40 promoter, the secreted luciferase gene, and the β-globin terminator sequence of nucleobase numbers 121 to 220. The PCR reaction performed cycles at 94° C. for 20 seconds, 60° C. for 30 seconds, and 68° C. for 2 minutes thirty times with the above-noted and a reaction solution composition.

4. Case where a shRNA-expressing DNA sequence is defined as the target RNA-expressing DNA sequence to be amplified:

A linear DNA was produced with the following method, the linear DNA including, in order, an hU6 promoter sequence, an EGFP shRNA-expressing DNA sequence as the shRNA-expressing DNA sequence, an annealed sequence, and the SV40 terminator sequence of nucleobase numbers 130 to 220.

4-1. Production of hU6 Promoter Sequence

Figure 19:
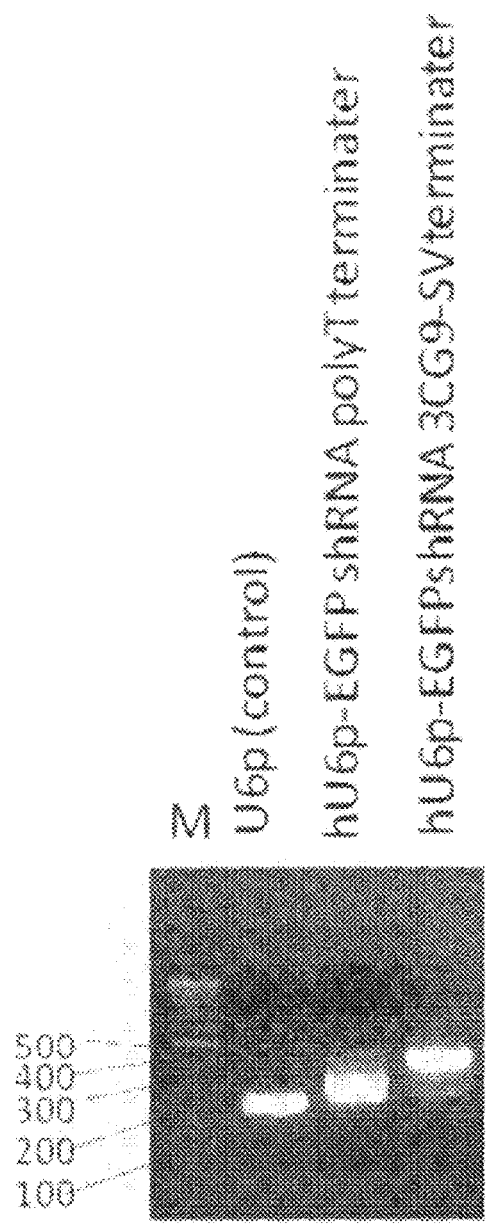
FIG. 19 shows results of agarose electrophoresis of the produced linear DNA for shRNA expression. M indicates a marker (bp).

With human genome (made by Promega Corporation) as a template, a human hU6 promoter was amplified using a forward primer shown in SEQ ID NO: 54 and a reverse primer shown in SEQ ID NO: 55. The PCR reaction was performed using GXL polymerase (made by Takara Bio Inc.) in adherence to the recommended protocol therefor. Final concentrations were adjusted to be, respectively, template: 50 pg/µL, forward primer: 0.3 µM, reverse primer: 0.3 µM, then cycles at 98° C. for 10 seconds, 60° C. for 15 seconds, and 68° C. for 30 seconds were carried out thirty times using an icycler thermal cycler (made by Bio-Rad). The linear DNA produced was confirmed with agarose electrophoresis, the results of which are shown in FIG. 19 (left lane).

4-2. Production of Linear DNA that Includes, in Order, hU6 Promoter Sequence, EGFP shRNA-expressing DNA Sequence, and Annealed Sequence (3GC9)

Using the hU6 promoter produced in 4-1 as the template, a linear DNA was produced with the PCR method employing a forward primer shown in SEQ ID NO: 54 and a reverse primer shown in SEQ ID NO: 57, the linear DNA including, in order, the hU6 promoter sequence, the EGFP shRNA-expressing DNA sequence, and the annealed sequence (3GC9). In the PCR reaction, final concentrations were adjusted to be, respectively, template: 50 pg/µL, forward primer: 0.3 µM, reverse primer: 0.3 µM, then cycles at 98° C. for 10 seconds, 60° C. for 15 seconds, and 68° C. for 45 seconds were carried out thirty times using an icycler thermal cycler (made by Bio-Rad).

4-3. Production of Linear DNA that Includes, in Order, hU6 Promoter Sequence, EGFP shRNA-expressing DNA Sequence, Annealed Sequence (3GC9), and SV40 Terminator Sequence Using the hU6 promoter sequence, EGFP shRNA-expressing DNA sequence, and annealed sequence (3GC9) produced in 4-2 as the template, a linear DNA was produced with the PCR method by employing a forward primer shown in SEQ ID NO: 54 and a reverse primer shown in SEQ ID NO: 50, the linear DNA including, in order, the hU6 promoter sequence, the EGFP shRNA-expressing DNA sequence, the annealed sequence (3GC9), and the SV40 terminator sequence. In the PCR reaction, final concentrations were adjusted to be, respectively, template: 50 pg/µL, forward primer: 0.3 µM, reverse primer: 0.3 µM, then cycles at 98° C. for 10 seconds, 60° C. for 15 seconds, and 68° C. for 45 seconds were carried out thirty times using an icycler thermal cycler (made by Bio-Rad). The linear DNA produced was confirmed with agarose electrophoresis, the results of which are shown in FIG. 19 (right lane).

4-4. Production of Linear DNA that Includes, in Order, hU6 Promoter Sequence, EGFP shRNA-expressing DNA Sequence, and Poly-T Terminator Sequence A linear DNA was produced using a poly-T terminator, which is generally used as a terminator in place of the SV40 terminator when performing shRNA expression. Using the hU6 promoter sequence produced in 4-1 as the template, a linear DNA was produced with the PCR method by employing a forward primer shown in SEQ ID NO: 54 and a reverse primer shown in SEQ ID NO: 56, the linear DNA including, in order, the hU6 promoter sequence, the EGFP shRNA-expressing DNA sequence, and the poly-T terminator sequence. In the PCR reaction, final concentrations were adjusted to be, respectively, template: 50 pg/µL, forward primer: 0.3 µM, reverse primer: 0.3 µM, then cycles at 98° C. for 10 seconds, 60° C. for 15 seconds, and 68° C. for 45 seconds were carried out thirty times using an icycler thermal cycler (made by Bio-Rad). The linear DNA produced was confirmed with agarose electrophoresis, the results of which are shown in FIG. 19 (center lane).

4-5. Transfection into HEK 293 Cells pEGFP-C1 (made by Clontech) in an amount of 12.5 ng/well and the three linear DNAs produced, each in an amount of 50 ng/well, were transfected to HEK 293 cells using a FuGENE® HD Transfection Reagent kit (made by Roche), then observed under fluorescent light after 48 hours (FIG. 20). As a result, fluorescence was observed in a case where only the hU6 promoter sequence was transfected (top row in FIG. 20). Fluorescence was no longer observed in a case where the linear DNA including, in order, the hU6 promoter sequence, the EGFP shRNA-expressing DNA sequence, the annealed sequence (3GC9), and the SV40 terminator sequence was transfected (bottom row in FIG. 20). It was thus confirmed that EGFP shRNA was expressed by using the EGFP shRNA-expressing DNA sequence as the target RNA-expressing DNA sequence; that, as a result, EGFP siRNA (short interfering RNA) was produced; and that EGFP expression could be suppressed. Fluorescence was suppressed even in a case of transfecting the linear DNA including, in order, the hU6 promoter sequence, the EGFP shRNA-expressing DNA sequence, and the poly-T terminator sequence. There was even less fluorescence in a case of transfecting the linear DNA including, in order, the hU6 promoter sequence, the EGFP shRNA-expressing DNA sequence, the annealed sequence (3GC9), and the SV40 terminator sequence (middle row in FIG. 20), and a strong suppressive effect on protein expression was demonstrated with the linear DNA of the present invention.

INDUSTRIAL APPLICABILITY

The present invention can be preferably employed in a technical field such as RNA expression in cell culture, RNA expression using linear DNA, and the like, or in a field such as screening that employs RNA expression in cell culture.

The invention claimed is:

1. An artificially synthesized double-stranded linear DNA for RNA expression in cells comprising, in order, a promoter sequence, a target RNA-expressing DNA sequence, and a heterologous 30-200 nucleobase terminator sequence, wherein the terminator sequence comprises at least a 30-nucleobase portion of SEQ ID NO: 1 and wherein the terminator sequence includes a sequence of nine connected nucleobases: (A/T/G), (A/T/G), T, A, A, A, (A/T/G/C), (A/T/G/C), (A/G/C).

2. The linear DNA according to claim 1, wherein the target RNA-expressing DNA sequence is a shRNA-expressing DNA sequence.

3. The linear DNA according to claim 1, wherein the terminator sequence comprises SEQ ID NO: 1.

4. The linear DNA according to claim 3, wherein the target RNA-expressing DNA sequence is a shRNA-expressing DNA sequence.

5. The linear DNA according to claim 1, wherein the terminator sequence comprises SEQ ID NO: 31.

6. The linear DNA according to claim 5, wherein the target RNA-expressing DNA sequence is a shRNA-expressing DNA sequence.

7. A method for RNA expression, comprising transfecting the linear DNA according to claim 6 into a cell and expressing RNA from the linear DNA.

* * * * *